US008989867B2

(12) United States Patent
Chow et al.

(10) Patent No.: US 8,989,867 B2
(45) Date of Patent: Mar. 24, 2015

(54) IMPLANTABLE NERVE WRAP FOR NERVE STIMULATION CONFIGURED FOR FAR FIELD RADIATIVE POWERING

(75) Inventors: Eric Y. Chow, Houston, TX (US); Milton M. Morris, Bellaire, TX (US); David L. Thompson, Houston, TX (US)

(73) Assignee: Cyberonics, Inc., Houston, TX (US)

( * ) Notice: Subject to any disclaimer, the term of this patent is extended or adjusted under 35 U.S.C. 154(b) by 0 days.

(21) Appl. No.: 13/434,119

(22) Filed: Mar. 29, 2012

(65) Prior Publication Data
US 2013/0018439 A1 Jan. 17, 2013

Related U.S. Application Data

(60) Provisional application No. 61/507,992, filed on Jul. 14, 2011.

(51) Int. Cl.
A61N 1/00 (2006.01)
A61N 1/378 (2006.01)
A61N 1/36 (2006.01)

(52) U.S. Cl.
CPC .......... *A61N 1/3787* (2013.01); *A61N 1/3605* (2013.01)
USPC .......................................................... 607/60

(58) Field of Classification Search
USPC .......................................................... 607/60
See application file for complete search history.

(56) References Cited

U.S. PATENT DOCUMENTS

| 3,867,950 | A | 2/1975 | Fischell | |
|---|---|---|---|---|
| 6,289,238 | B1 | 9/2001 | Besson | |
| 7,245,117 | B1 | 7/2007 | Joy | |
| 7,481,771 | B2 | 1/2009 | Fonseca | |
| 7,725,195 | B2 * | 5/2010 | Lima et al. | 607/60 |
| 8,634,928 | B1 * | 1/2014 | O'Driscoll et al. | 607/61 |
| 2003/0171792 | A1 * | 9/2003 | Zarinetchi et al. | 607/61 |
| 2006/0232408 | A1 * | 10/2006 | Nycz et al. | 340/572.1 |
| 2007/0055308 | A1 | 3/2007 | Haller et al. | |

(Continued)

FOREIGN PATENT DOCUMENTS

WO 2010104569 A1 9/2010

OTHER PUBLICATIONS

International Patent Application No. PCT/US2012/032009, International Search Report and Written Opinion Dated Jun. 13, 2012, 13 pages.

Sun, X. et al.; "Design of Several Key Circuits of UHF Passive RFID Tag"; *China Integrated Circuit*, vol. 16, 2007 (Institute of Microelectronics of Tsinghua University); found at: http://en.cnki.com.cn/Article_en/CJFDTOTAL-JCDI200701009.htm.

(Continued)

*Primary Examiner* — Eric D. Bertram
(74) *Attorney, Agent, or Firm* — Cyberonics, Inc.

(57) ABSTRACT

A particular implantable device may include an antenna configured to receive a far field radiative signal. The implantable device may also include a voltage rectifier configured to rectify the far field radiative signal received by the antenna to provide a rectified voltage signal. The implantable device may further include a charge storage element operative to receive the rectified voltage signal and to store charge responsive to the rectified voltage signal. The implantable device may also include a stimulation module powered by the charge storage element. The stimulation module may be operative to generate an electrical stimulation signal to stimulate a target nerve of a patient. The implantable medical device may further include a nerve wrap configured to house the voltage rectifier, the charge storage element, and the stimulation module. The nerve wrap may include one or more electrodes operative to deliver the electrical stimulation signal to the target nerve.

27 Claims, 7 Drawing Sheets

(56) References Cited

U.S. PATENT DOCUMENTS

| | | |
|---|---|---|
| 2008/0108915 A1 | 5/2008 | Penner |
| 2009/0069648 A1 | 3/2009 | Irazoqui et al. |
| 2009/0105782 A1* | 4/2009 | Mickle et al. ............... 607/45 |
| 2010/0010565 A1 | 1/2010 | Lichtenstein et al. |
| 2010/0179449 A1 | 7/2010 | Chow et al. |
| 2010/0228308 A1 | 9/2010 | Cowan et al. |
| 2013/0018438 A1 | 1/2013 | Chow et al. |
| 2013/0018439 A1 | 1/2013 | Chow et al. |
| 2013/0018440 A1 | 1/2013 | Chow et al. |
| 2013/0261703 A1 | 10/2013 | Chow et al. |

OTHER PUBLICATIONS

"Part 15—Radio Frequency Devices (47 CFR 15), Title 47 of the Code of Federal Regulations," *Federal Communications Commission*, current as of Dec. 22, 2011; found at: http://www.ecfr.gov/cgi-bin/text-idx?node=47:1.0.1.1.16.

Akkermans, J.A.G. et al., "Analytical models for low-power rectenna design," Antennas and Wireless Propagation Letters, IEEE, vol. 4, No., pp. 187-190, 2005 doi: 10.1109/LAWP.2005.850798; found at: http://ieeexplore.ieee.org/stamp/stamp.jsp?tp=&arnumber=1435362&isnumber=30362.

Baker, M.W. et al., "Feedback Analysis and Design of RF Power Links for Low-Power Bionic Systems," Biomedical Circuits and Systems, IEEE Transactions on, vol. 1, No. 1, pp. 28-38, Mar. 2007; doi 10.1109/TBCAS.2007.893180; found at: http://ieeexplore.ieee.org/stamp/stamp.jsp?tp=&arnumber=4156129&isnumber=4156127.

Balanis, C. A., *Advanced Engineering Electromagnetics*. New York: Wiley, 1989, pp. 39-98, and 123-258.

Brown, W.C., "The History of Power Transmission by Radio Waves," *Microwave Theory and Techniques, IEEE Transactions on*, vol. 32, pp. 1230-1242, 1984.

Chaimanonart, N.; et al., "Remote RF powering system for wireless MEMS strain sensors," Sensors Journal, IEEE, vol. 6, No. 2, pp. 484-489, Apr. 2006; doi: 10.1109/JSEN.2006.870158; found at: http://ieeexplore.ieee.org/stamp/stamp.jsp?tp=&arnumber=1608093&isnumber=33774.

Chen, Z.N. et al., "Small Printed Ultrawideband Antenna With Reduced Ground Plane Effect," *Antennas and Propagation, IEEE Transactions on*, vol. 55, pp. 383-388, 2007.

Cheng, S. et al., "Printed Slot Planar Inverted Cone Antenna for Ultrawideband Applications," *Antennas and Wireless Propagation Letters, IEEE*, vol. 7, pp. 18-21, 2008.

Chow, E. et al., "Evaluation of Cardiovascular Stents as Antennas for Implantable Wireless Applications," *Microwave Theory and Techniques, IEEE Transactions on*, vol. 57, pp. 2523-2532, 2009.

Chow, E. Y. et al., "A Miniature-Implantable RF-Wireless Active Glaucoma Intraocular Pressure Monitor," *Biomedical Circuits and Systems, IEEE Transactions on*, vol. 4, pp. 340-349, 2010.

Chow, E.Y. et al., "Fully Wireless Implantable Cardiovascular Pressure Monitor Integrated with a Medical Stent," *Biomedical Engineering, IEEE Transactions on*, vol. 57, pp. 1487-1496, 2010.

Chow, E. Y. et al., "High Data-Rate 6.7 GHz Wireless Asic Transmitter for Neural Prostheses," in *Engineering in Medicine and Biology Society, 2007. EMBS 2007. 29th Annual International Conference of the IEEE*, 2007, pp. 6580-6583.

Chow, E. Y. et al., "High frequency transcutaneous transmission using stents configured as a dipole radiator for cardiovascular implantable devices," in *Microwave Symposium Digest, 2009. MTT '09. IEEE MTT-S International*, 2009, pp. 1317-1320.

Chow, E. Y. et al., "Implantable Wireless Telemetry Boards for in Vivo Transocular Transmission," *Microwave Theory and Techniques, IEEE Transactions on*, vol. 56, pp. 3200-3208, 2008.

Chow, E. Y. et al., "Miniature antenna for RF telemetry through ocular tissue," in *Microwave Symposium Digest, 2008 IEEE MTT-S International*, 2008, pp. 1309-1312.

Chow, E. Y. et al., "Mixed-signal integrated circuits for self-contained sub-cubic millimeter biomedical implants," in *Solid-State Circuits Conference Digest of Technical Papers (ISSCC), 2010 IEEE International*, 2011, pp. 236-237.

Chow, E. Y. et al., "Toward an Implantable Wireless Cardiac Monitoring Platform Integrated with an FDA-Approved Cardiovascular Stent," *Journal of Interventional Cardiology*, vol. 22, pp. 479-487, 2009.

Chow, E. Y. et al.,, "Sub-cubic millimeter intraocular pressure monitoring implant to enable genetic studies on pressure-induced neurodegeneration," in *Engineering in Medicine and Biology Society (EMBC), 2010 Annual International Conference of the IEEE*, 2010, pp. 6429-6432.

Chow, E. Y. et al.; "Chapter 9: Wireless Powering and Propagation of Radio Frequencies through Tissue," in *Wireless Power Transfer*, J. Agbinya, Ed., Aalborg, Denmark: River Publishers, Jul. 2012, pp. 301-336.

Chow, E.Y. et al., "Wireless Powering and the Study of RF Propagation Through Ocular Tissue for Development of Implantable Sensors," *Antennas and Propagation, IEEE Transactions on*, vol. 59, pp. 2379-2387, 2011.

Curty, Jari-Pascal et al., A Model for—Power Rectifier Analysis and Design, IEEE Transactions on Circuits and Systems—I: Regular Papers, vol. 52, No. 12, Dec. 2005, pp. 2771-2779.

Dolgov, A.; et al., "Power Management System for Online Low Power RF Energy Harvesting Optimization," Circuits and Systems I: Regular Papers, IEEE Transactions on, vol. 57, No. 7, pp. 1802-1811, Jul. 2010; doi: 10.1109/TCSI.2009.2034891; found at: http://ieeexplore.ieee.org/stamp/stamp.jsp?tp=&arnumber=5395599&isnumber=5512812.

Douyere, A. et al., "High efficiency microwave rectenna circuit: modelling and design," Electronics Letters, vol. 44, No. 24, pp. 1409-1410, Nov. 20, 2008 doi: 10.1049/e1:20081794 URL: http://ieeexplore.ieee.org/stamp/stamp.jsp?tp=&arnumber=4689488&isnumber=4689470.

Everhart, E. et al.; The Cockcroft Walton Voltage Multiplying Circuit Rev. Sci. Instrum. 25, 394 (1954); found at: http://rsi.aip.org/resource/1/rsinak/v25/i4/p394_s1 ?isAuthorized =no.

Fischell, R.E., "The retrospectroscope-the invention of the rechargeable cardiac pacemaker: vignette #9," *Engineering in Medicine and Biology Magazine, IEEE*, vol. 9, pp. 77-78, 1990.

Gabriel, C. et al., "Compilation of the dielectric properties of body tissues at RF and microwave frequencies," *Report N.AL/OE-TR-1996-0037, Occupational and environmental health directorate, Radiofrequency Radiation Division, Brooks Air Force Base*, Texas (USA), 1996.

Gabriel, C. et al., "The dielectric properties of biological tissues: I. Literature survey." vol. 41, 1996, p. 2231.

Gabriel, S. et al., "The dielectric properties of biological tissues: II. Measurements in the frequency range 10 Hz to 20 GHz." vol. 41, 1996, p. 2251.

Gabriel, S. et al., "The dielectric properties of biological tissues: III. Parametric models for the dielectric spectrum of tissues." vol. 41, 1996, p. 2271.

Glaser, P., "Satellite solar power station and microwave transmission to earth," *Journal of Microwave Power*, vol. 5, 1970.

Hagerty, J.A. et al., "Recycling ambient microwave energy with broad-band rectenna arrays," Microwave Theory and Techniques, IEEE Transactions on, vol. 52, No. 3, pp. 1014-1024, Mar. 2004 doi: 10.1109/TMTT.2004.823585 found at: http://ieeexplore.ieee.org/stamp/stamp.jsp?tp=&arnumber=1273745&isnumber=28503.

Humayun, M.S., et al., "Visual perception in a blind subject with a chronic microelectronic retinal prosthesis," *Vision Research*, vol. 43, pp. 2573-2581, 2003.

ICNIRP, "Guidelines for limiting exposure to time-varying electric, magnetic and electromagnetic fields (up to 200 GHz)," *Health Physics*, vol. 74, pp. 494-522, 1998.

ICNIRP, "Guidelines for limiting exposure to time-varying electric and magnetic fields (1 Hz to 100 kHz)," *Health Physics*, vol. 99, pp. 818-836, 2010.

ICNIRP, "Guidelines for limiting exposure to time-varying electric, magnetic, and electromagnetic fields (up to 300 GHz)," *Health Phys.*, vol. 74, pp. 494-522, 1998.

(56) References Cited

OTHER PUBLICATIONS

Joshi, R. K. et al., "Printed wideband variable strip width loop antenna," in *Antennas and Propagation Society International Symposium, 2007 IEEE*, 2007, pp. 4793-4796.

Karacolak, T. et al., "Design of a Dual-Band Implantable Antenna and Development of Skin Mimicking Gels for Continuous Glucose Monitoring," *Microwave Theory and Techniques, IEEE Transactions on*, vol. 56, pp. 1001-1008, 2008.

Knapp, J.P., "Ansys Inc. Request for Waiver of 47 C.F.R. § 1.1307(b)(2) of Commission Rules, DA 11-192," Federal Communications Commission, 2011.

Lin, Yi-Cheng. et al., "Compact Ultrawideband Rectangular Aperture Antenna and Band-Notched Designs," *Antennas and Propagation, IEEE Transactions on*, vol. 54, pp. 3075-3081, 2006.

Ling, Ching-Wei et al., "A Simple Printed Ultrawideband Antenna With a Quasi-Transmission Line Section," *Antennas and Propagation, IEEE Transactions on*, vol. 57, pp. 3333-3336, 2009.

Margalit, E., et al., "Retinal Prosthesis for the Blind," *Survey of Ophthalmology*, vol. 47, pp. 335-356, 2002.

Means, D. L. et al., "Evaluating Compliance with FCC Guidelines for Human Exposure to Radiofrequency Electromagnetic Fields," *OET Bulletin 65 (Edition 97-01) Supplement C (Edition 01-01), Federal Communications Commission Office of Engineering & Technology*, 2001.

Najafi, N. et al., "Initial Animal Studies of a Wireless, Batteryless, MEMS Implant for Cardiovascular Applications " *Biomedical Microdevices*, vol. 6, pp. 61-65, 2004.

Ogden, C. L., et al., "Mean Body Weight, Height, and Body Mass Index, United States 1960-2002," *Centers for Disease Control and Prevention*, vol. 347, 2004.

Paing, T. et al., "Resistor Emulation Approach to Low-Power RF Energy Harvesting," Power Electronics, IEEE Transactions on, vol. 23, No. 3, pp. 1494-1501, May 2008 doi: 10.1109/TPEL.2008.921167; found at: http://ieeexplore.ieee.org/stamp/stamp.jsp?tp=&arnumber=4492966&isnumber=4509502.

Ramo, S. et al., *Fields and Waves in Communication Electronics*, 3rd ed.: John Wiley & Sons, Inc., 1994, pp. 274-313, 584-668, 667-733.

Ren, Yu-Jiun et al., "5.8-GHz circularly polarized dual-diode rectenna and rectenna array for microwave power transmission," Microwave Theory and Techniques, IEEE Transactions on, vol. 54, No. 4, pp. 1495-1502, Jun. 2006; doi: 10.1109/TMTT.2006.871362; found at: http://ieeexplore.ieee.org/stamp/stamp.jsp?tp=&arnumber=1618568&isnumber=33917.

Ritzema, J. et al., "Direct Left Atrial Pressure Monitoring in Ambulatory Heart Failure Patients," *Circulation*, vol. 116, pp. 2952-2959, 2007.

Soontornpipit, P. et al., "Design of implantable microstrip antenna for communication with medical implants," *Microwave Theory and Techniques, IEEE Transactions on*, vol. 52, pp. 1944-1951, 2004.

Sze, Jia-Yi et al., "Design of Band-Notched Ultrawideband Square Aperture Antenna With a Hat-Shaped Back-Patch," *Antennas and Propagation, IEEE Transactions on*, vol. 56, pp. 3311-3314, 2008.

Tesla, Nikola; Colorado Springs Notes 1899-1900; found at: http://www.scribd.com/doc/41567714/Nikola-Tesla-Colorado-Springs-Notes-1899-1900.

Yanai, D., et al., "Visual Performance Using a Retinal Prosthesis in Three Subjects With Retinitis Pigmentosa," *American Journal of Ophthalmology*, vol. 143, pp. 820-827.e2, 2007.

Yazdanboost, K.Y. et al., "Ultra wideband L-loop antenna," in *Ultra-Wideband, 2005. ICU 2005. 2005 IEEE International Conference on*, 2005, pp. 201-205.

Zbitou, J.; et al., "Hybrid rectenna and monolithic integrated zero-bias microwave rectifier," Microwave Theory and Techniques, IEEE Transactions on, vol. 54, No. 1, pp. 147-152, Jan. 2006 doi: 10.1109/TMTT.2005.860509 found at: URL: http://ieeexplore.ieee.org/stamp/stamp.jsp?tp=&arnumber=1573807&isnumber=33279.

Zhang, Jin-Ping. et al., "Microstrip-Fed Semi-Elliptical Dipole Antennas for Ultrawideband Communications," *Antennas and Propagation, IEEE Transactions on*, vol. 56, pp. 241-244, 2008.

"SOLX, Inc.," found at: http://www.solx.com/; 2011; printed on Aug. 14, 2014.

Nazli, H. et al., "An Improved Design of Planar Elliptical Dipole Antenna for UWB Applications," *Antennas and Wireless Propagation Letters, IEEE*, vol. 9, pp. 264-267, 2010.

Ojaroudi, M. et al., "Small Square Monopole Antenna With Enhanced Bandwidth by Using Inverted T-Shaped Slot and Conductor-Backed Plane," *Antennas and Propagation, IEEE Transactions on*, vol. 59, pp. 670-674, Feb. 2011.

Oraizi, H. et al., "Miniaturized UWB Monopole Microstrip Antenna Design by the Combination of Giusepe Peano and Sierpinski Carpet Fractals," *Antennas and Wireless Propagation Letters, IEEE*, vol. 10, pp. 67-70, 2011.

Ryu, K. S. et al., "UWB Dielectric Resonator Antenna Having Consistent Omnidirectional Pattern and Low Cross-Polarization Characteristics," *Antennas and Propagation, IEEE Transactions on*, vol. 59, pp. 1403-1408, Apr. 2011.

Thomas, K. G., et al., "A Simple Ultrawideband Planar Rectangular Printed Antenna With Band Dispensation," *Antennas and Propagation, IEEE Transactions on*, vol. 58, pp. 27-34, Jan. 2010.

* cited by examiner

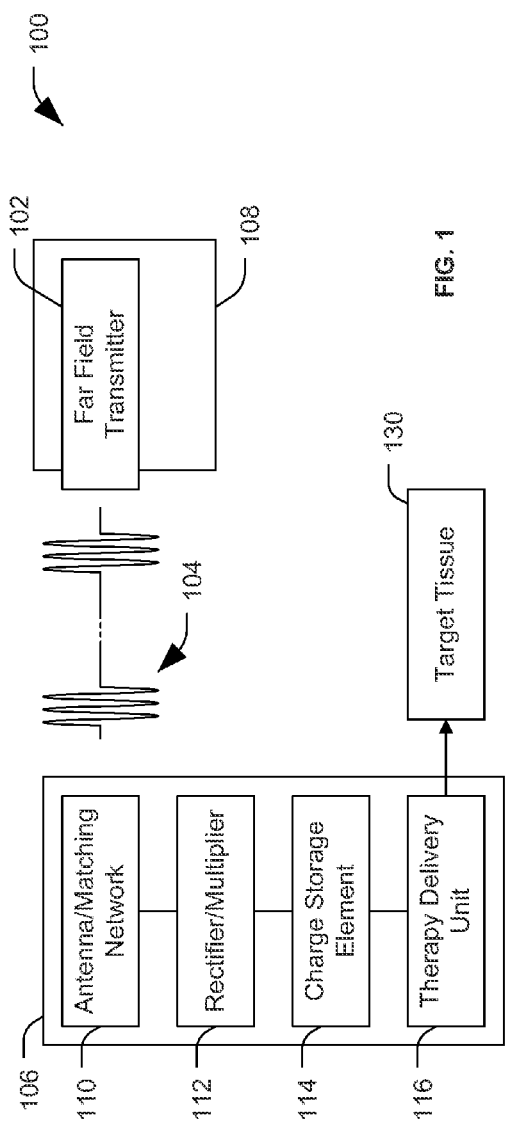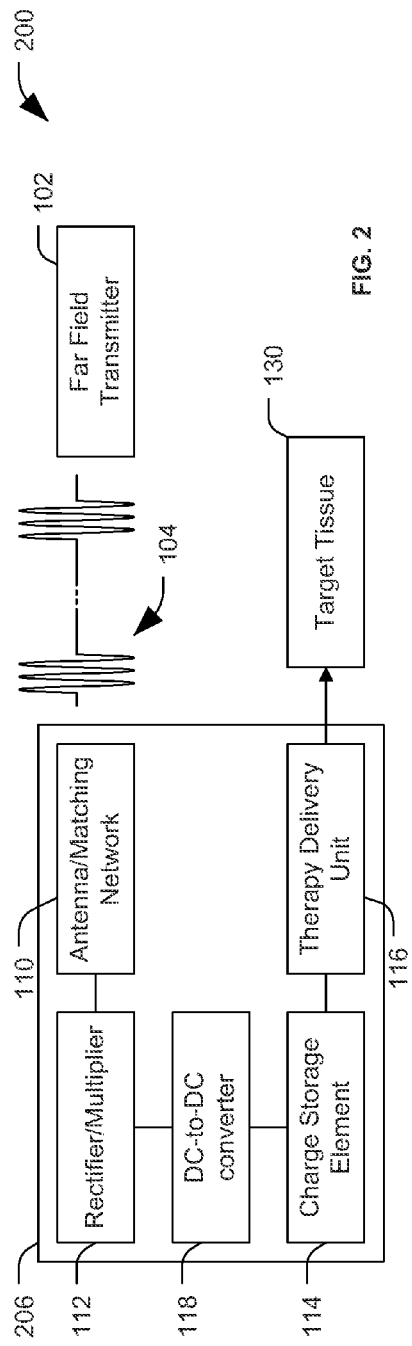

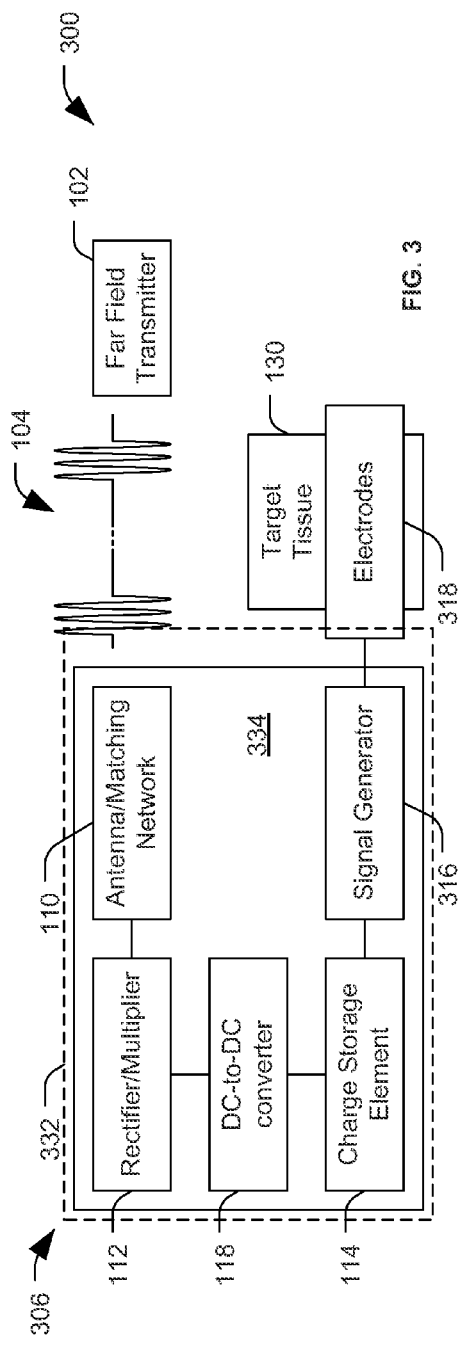
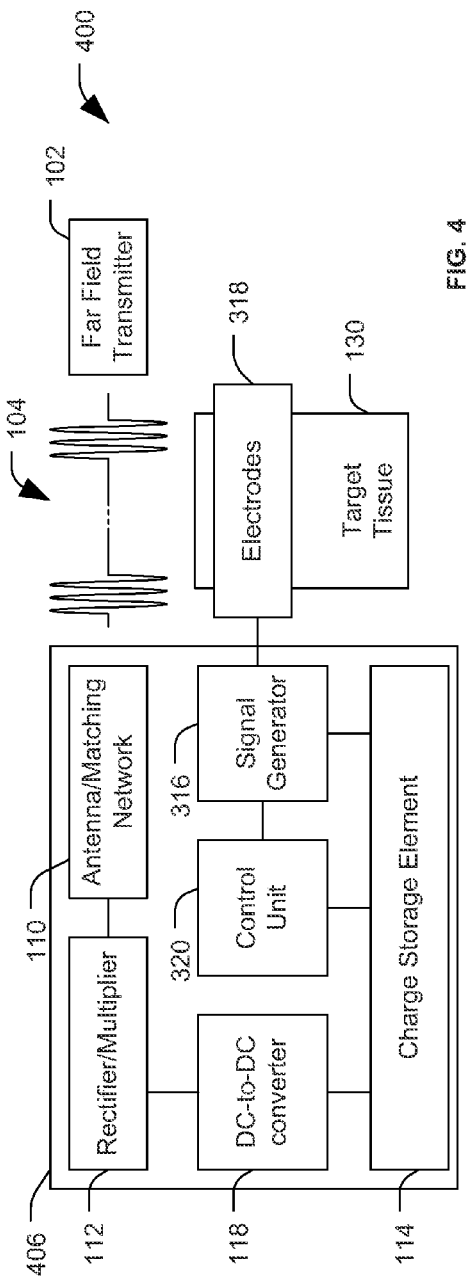

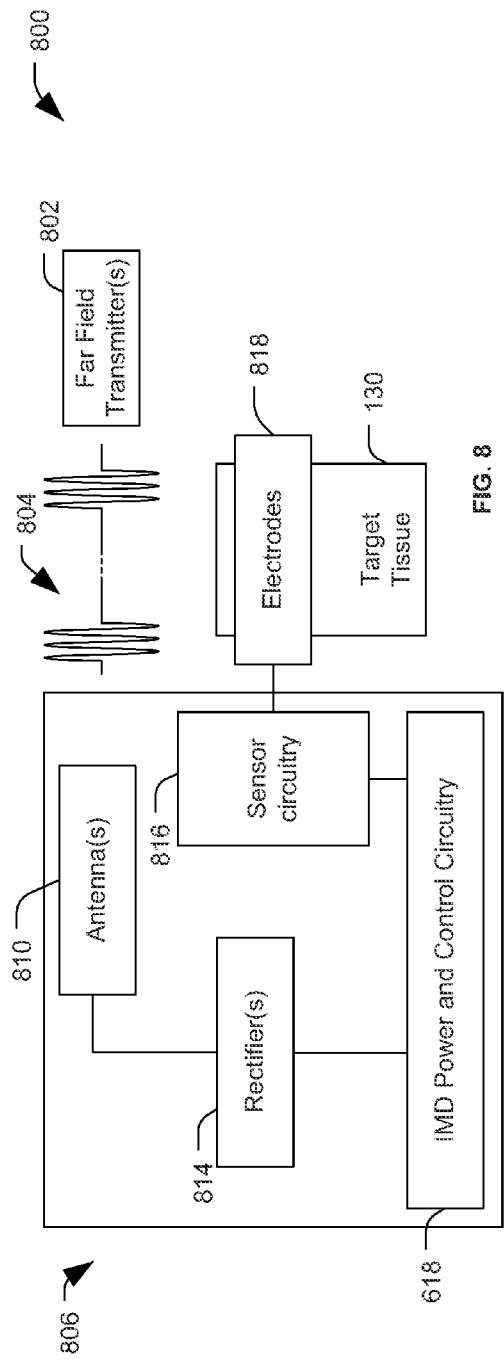
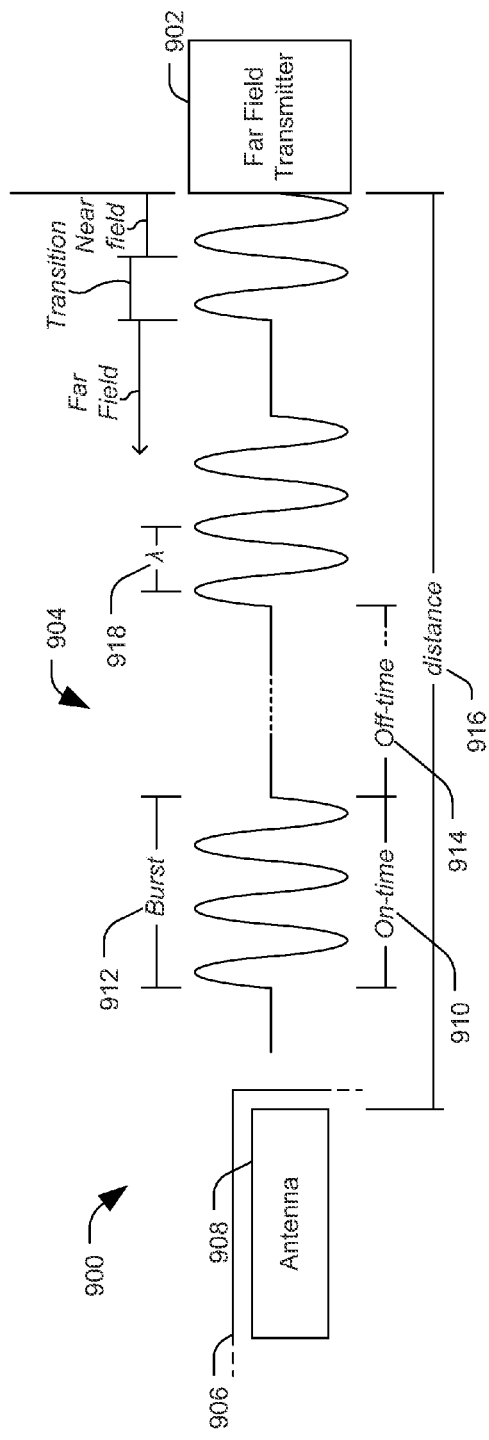

IMPLANTABLE NERVE WRAP FOR NERVE STIMULATION CONFIGURED FOR FAR FIELD RADIATIVE POWERING

CROSS-REFERENCE TO RELATED APPLICATIONS

This application claims priority to U.S. Provisional Application No. 61/507,992, filed on Jul. 14, 2011 and entitled "ULTRA-MINIATURE LEADLESS PULSE GENERATOR FOR IMPLANTATION NEXT TO THE VAGUS NERVE IN THE NECK," the contents of which are hereby incorporated by reference in their entirety. This application also may contain subject matter that may relate to the following commonly assigned co-pending applications incorporated herein by reference: "FAR FIELD RADIATIVE POWERING OF IMPLANTABLE MEDICAL THERAPY DELIVERY DEVICES," Ser. No. 13/433,907, filed Mar. 29, 2012; and "POWERING OF AN IMPLANTABLE MEDICAL THERAPY DELIVERY DEVICE USING FAR FIELD RADIATIVE POWERING AT MULTIPLE FREQUENCIES," Ser. No. 13/434,240, filed Mar. 29, 2012;

FIELD OF THE DISCLOSURE

The present disclosure is generally related to far field radiative powering of implantable medical devices.

BACKGROUND

Powering implantable medical devices can be problematic. Many implantable medical devices include a battery. If the battery is rechargeable, the implantable medical device may include charging components to receive power from an external source to recharge the battery. For example, the implantable medical device may include a coil that is operative to inductively couple with an external coil. Providing power via inductive coupling may require that the coil of the implantable medical device and the external coil be relatively close to one another (e.g., within a distance over which a magnetic field is relatively strong). Further, inductive coupling may be less efficient when the coil of the implantable medical device and the external coil are not aligned or oriented properly.

SUMMARY

In a particular embodiment, an implantable medical device may include an antenna configured to receive a far field radiative signal. The implantable medical device may also include a voltage rectifier configured to rectify the far field radiative signal received by the antenna to provide a rectified voltage signal. The implantable medical device may further include a charge storage element operative to receive the rectified voltage signal and to store charge responsive to the rectified voltage signal. The implantable medical device may also include a stimulation module powered by the charge storage element. The stimulation module may be operative to generate an electrical stimulation signal to stimulate a target nerve (e.g., a vagus nerve, a trigeminal nerve, a glossopharyngeal nerve, or a hypoglossal nerve) of a patient. The implantable medical device may further include a nerve wrap configured to house the voltage rectifier, the charge storage element, and the stimulation module. The nerve wrap may include one or more electrodes operative to deliver the electrical stimulation signal to the target nerve.

In a particular embodiment, an implantable medical device includes an antenna configured to receive a far field radiative signal. The implantable medical device may also include a voltage rectifier configured to rectify the far field radiative signal received by the antenna to provide a rectified voltage signal. The implantable medical device may also include a charge storage element operative to receive the rectified voltage signal and to store charge responsive to the rectified voltage signal. The implantable medical device may also include a stimulation module powered by the charge storage element. The stimulation module may be operative to generate an electrical stimulation signal to stimulate a target nerve of a patient. The implantable medical device may further include a nerve wrap configured to couple to the target nerve. The nerve wrap may include proximity electrodes operative to deliver the electrical stimulation signal to the target nerve. The implantable medical device may also include a flexible printed circuit board. The voltage rectifier, the charge storage element, and the stimulation module may be integrated on the flexible printed circuit board. The flexible printed circuit board may be embedded in the nerve wrap.

In a particular embodiment, a system includes an external transmitter configured to transmit a far field radiative signal and an implantable medical device that includes an antenna configured to receive the far field radiative signal. The implantable medical device may include a charge storage element that is operative to store a charge responsive to the received far field radiative signal. The implantable medical device may further include a pulse generator that may be powered by the charge storage element and that may be operative to generate an electrical stimulation signal to stimulate a target tissue of a patient. The implantable medical device may include a nerve wrap configured to couple to the target tissue. The nerve wrap may include proximity electrodes operative to deliver the electrical stimulation signal to the target tissue. The implantable medical device may also include a flexible printed circuit board. The flexible printed circuit board may be embedded in the nerve wrap. The charge storage element and the pulse generator may be integrated on the flexible printed circuit board.

The features, functions, and advantages that have been described can be achieved independently in various embodiments or may be combined in yet other embodiments, further details of which are disclosed with reference to the following description and drawings.

BRIEF DESCRIPTION OF THE DRAWINGS

FIG. 1 is a block diagram of a first particular embodiment of a system including an implantable medical device and a far field transmitter;

FIG. 2 is a block diagram of a second particular embodiment of a system including an implantable medical device and a far field transmitter;

FIG. 3 is a block diagram of a third particular embodiment of a system including an implantable medical device and a far field transmitter;

FIG. 4 is a block diagram of a fourth particular embodiment of a system including an implantable medical device and a far field transmitter;

FIG. 8 is a block diagram of an eighth particular embodiment of a system including an implantable medical device and a far field transmitter;

FIG. 9 is diagram illustrating a particular embodiment of powering an implantable medical device using a far field transmitter;

DETAILED DESCRIPTION

Figure 5:
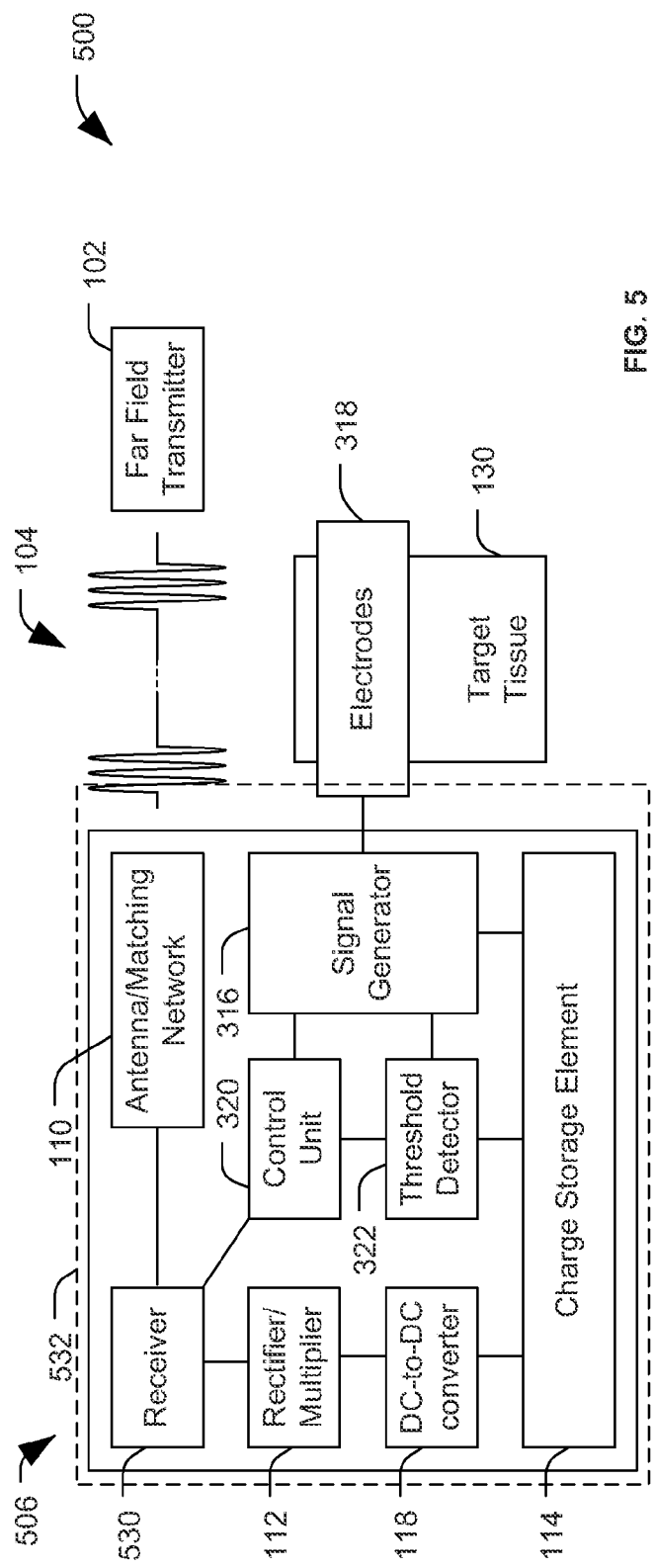
FIG. 5 is a block diagram of a fifth particular embodiment of a system including an implantable medical device and a far field transmitter.

Disclosed systems, methods and devices enable powering of implantable medical devices using far-field radiative signals. Using far field radiative signals to power an implantable medical device may enable miniaturization of the implantable medical device since no onboard power storage (or no long-term onboard power storage) is required. Far field radiative powering, especially in combination with miniaturization of the implantable medical device, may enable use of reduced complexity procedures to implant the implantable medical device and may enable use of the implantable medical device in new areas of the body. Particular embodiments may provide effective screening tools to determine whether a particular type of treatment will be effective for a particular patient.

Disclosed implantable medical devices may be used to treat various conditions by applying treatment to one or more tissues of a patient's body. To illustrate, an implantable medical device may be used to target neural tissue by inducing efferent or afferent action potentials in the neural tissue or by blocking intrinsic efferent or afferent action potentials in the neural tissue. For example, the implantable medical device may be used to target a vagus or trigeminal nerve to treat one or more conditions, such as epilepsy or other seizure inducing conditions. In another example, the implantable medical device may target an optic nerve to treat a vision condition or to supplement or facilitate use of a visual prosthesis for sight restoration. In another example, the implantable medical device may target a hypoglossal nerve to treat one or more conditions, such as sleep apnea. Although the examples above each relate to cranial nerves, the implantable medical device may be used to target another nerve or set of nerves rather than or in addition to a cranial nerve. For example, the implantable medical device may be used to target a sacral nerve to treat one or more conditions, such as to facilitate bladder control. In another example, the implantable medical device may be used to target a phrenic nerve to treat one or more conditions, such as to facilitate diaphragm or respiration control. In another example, the implantable medical device may be used to target one or more nerves of the spinal cord to treat one or more conditions, such as to facilitate pain management. Further, in addition to or instead of targeting a neural tissue, the implantable medical device may be used to target other tissue of a patient's body. For example, the implantable medical device may be used to stimulate a muscle to induce muscle contraction. To illustrate, the implantable medical device may target a heart muscle to act as a pacemaker. Other examples of conditions that may be treated using an implantable medical device that is at least partially powered by far field radiative power include, but are not limited to, traumatic brain injury and depression.

FIG. 1 is a block diagram of a first particular embodiment of a system 100 including an implantable medical device 106 and an external device 108. The implantable medical device 106 may be wirelessly powered by the external device 108. For example, the external device 108 may emit electromagnetic energy by transmitting radio-frequency signals using an external antenna (e.g., the far field transmitter 102). At least a portion of the electromagnetic energy may be received by an antenna of the implantable medical device 106 as far field radiative signals 104. In another example, the implantable medical device 106 may receive energy via near-field signals (e.g., by inductive coupling of the antenna of the implantable medical device 106 and an antenna of the far field transmitter 102). In yet another example, the implantable medical device 106 may receive energy via near-field signals and via far field radiative signals 104, either simultaneously or at different times.

Electromagnetic energy may be described as propagating through a near field region in which the magnetic fields are relatively strong, a far field region in which the magnetic fields are relatively weak, and a transition region between the near field region and the far field region. Although there is no generally accepted firm boundary between these regions, as used herein, and as illustrated in FIG. 9, the near field region refers to a region within about one wavelength of a source of the electromagnetic energy (e.g., a transmitting antenna), and the far field region refers to a region two wavelength or more from the source of the electromagnetic energy. Thus, a magnetic field is likely to be insignificant in the far field region. Conversely, the magnetic field may dominate in the near field region. Non-radiative mechanisms, such as inductive or capacitive coupling, operate over a relatively short distance and may be used to transfer energy in the near field region. Non-radiative mechanisms generally operate based on the principle that a circulating current can produce a magnetic field component which can induce an opposing current in a nearby structure. The magnetic field dissipates rapidly with distance. Near-field interactions can be extremely complex because they are reactive. That is, a transmit structure and transmitted electromagnetic fields react to receive structures and electromagnetic absorption in the vicinity. Approximate relationships descriptive of the near field region indicate that the near-field magnetic field strength decreases with the inverse-cube of distance and the near-field electric field decreases with the inverse-square, and thus, the power density in the near field region decreases as the inverse of the distance to the fifth power. Accordingly, for sufficient distances (typically around a wavelength or greater) the power quickly reduces to negligible levels. In contrast, for far-field radiative power transfer, the receive structure and its absorption does not affect the transmitter structure or the power output from the transmitter structure. The electric and magnetic fields from far-field radiative power transfer are better understood and both are inversely proportional to the distance and thus, the power is inversely proportional to the distance squared in the far field region.

From a clinical perspective, using non-radiative energy transfer may place limitations on the mobility of the patient and may lead to user error in patient populations. For example, non-radiative energy transfer mechanisms operate over a relatively short range and therefore require relatively short distances between an implanted medical device and an external charging device, which may limit patient mobility. Further, power may only be efficiently transferred via a non-radiative mechanism when a receiving component of the implanted medical device has a particular orientation with respect to a transmitting component of the external charging device. Maintaining this orientation can be difficult when the patient is moving (even breathing), which may further limit the patient's mobility.

Far field radiative signals 104 may be used to transfer power over a greater distance using radiative mechanisms. For example, the far field radiative signals 104 may transmit energy through free space using electrical fields propagating between a broad-beam external antenna and an internal antenna of the implantable medical device 106. This arrangement may allow greater freedom of placement for the external device 108 with respect to the patient. To illustrate, the external device 108 may be worn by or carried by the patient or may be positioned near the patient. As an illustrative example, when the implantable medical device 106 is implanted in the neck of the patient, the external device 108 may be worn by the patient, such as near the patient's upper arm or around the patient's neck. In another illustrative example, the external device 108 may include or be included within a mounted or table top power source.

As further described below, the implantable medical device 106 may include an antenna to receive the far field radiative signals 104, a matching network to impedance match the antenna with other components of the implantable medical device 106, power processing elements (e.g., a rectifier, a voltage multiplier, a step-up regulator, etc.), a charge storage element 114, and a therapy deliver unit 116. The implantable medical device 106 may use power derived at least partially from the far field radiative signals 104 to deliver therapy to a patient.

In a particular embodiment, the implantable medical device 106 includes an antenna and an associated matching network. In the embodiment illustrated in FIG. 1, the antenna and the matching network are illustrated as a single antenna/matching network 110 component; however, in other embodiments, the antenna and the matching network may be separate components. Thus, the antenna may include, be included within, or be coupled to the matching network. The antenna may be a dipole antenna, a monopole antenna, a serpentine antenna, a slot antenna, a patch antenna, a plane-inverted-F antenna (PIFA), a helical antenna, a fractal antenna, a loop antenna, or an antenna with another form factor configured to receive the far field radiative signals 104. The matching network may be adapted to match impedance of the antenna to other components of the implantable medical device 106 to achieve high efficiency power transfer. For example, the resistance of the antenna may be relatively low (e.g., on the order of a few ohms for electrically-small antennas and up to 50 ohms for electrically-large antennas) and one or more other components of the implantable medical device 106 may have a comparatively high resistance (e.g., on the order of KOhms). To illustrate, the antenna may have an impedance with a real part of approximately 10 ohms or less. In another illustrative example, the antenna may have an impedance with a real part of approximately 50 ohms or less. The matching network may facilitate impedance matching from the relatively low resistance of the antenna to a relatively high resistance of some other components of the implantable medical device 106. For example, conjugate matching, i.e. equal real impedance (resistance) and equal in magnitude but opposite in sign imaginary impedance (reactance), may achieve optimal power transfer.

The far field radiative signals 104 may be relatively weak when received at the antenna of the implantable medical device 106. For example, due to regulatory and safety constraints, the far field radiative signals 104 may be transmitted at a relatively low transmission power, such as an instantaneous transmission power of 1 watt or less, or an instantaneous transmission power of 5 watts or less. In a particular embodiment, an amount of power transferred via the far field radiative signal 104 to the implantable medical device 106 can be increased by delivering the power using multiple frequencies or frequency bands, and/or by using multiple far field transmitters 102.

As explained above, the far field radiative signals 104 may be transmitted over a distance of at least twice a wavelength of the far field radiative signals 104. For example, the far field radiative signals 104 may be transmitted over a distance of several meters or less, such as one meter or less. The free-space path loss (FSPL) of the far field radiative signals 104 may be estimated as a function of the transmission power of the far field transmitter 102; the distance, d, between the far field transmitter 102 and the patient; and the frequency, f, of the far field radiative signals 104. In a particular embodiment, the far field radiative signals 104 have a frequency within a range of approximately 100 MHz to approximately 5.8 GHz. For example, the far field radiative signal may have a frequency at, or in a frequency band centered at, approximately 433 MHz, approximately 900 MHz, approximately 2.4 GHz, approximately 5.8 GHz, or another frequency within an unlicensed or licensed frequency spectrum.

Thus, free-space path loss of the far field radiative signals 104 may be significant. To illustrate, when the distance, d, between the far field transmitter 102 and the patient is about 1 meter and the far field radiative signals 104 have a frequency, f, of about 2.4 GHz, the free-space path loss (FSPL), assuming two isotropic antennas, may be approximately described by the following equation:

$$FSPL = \left(\frac{4\pi df}{c}\right)^2 = (32\pi d)^2 = (10,000).$$

Therefore, the FSPL is proportional to the square of the distance between the far field transmitter 102 and the patient. The power transfer efficiency is inversely proportional to the square of the distance between the far field transmitter 102 and the patient. The FSPL can also be provided in decibels as shown by the following equation:

$$FSPL(dB) = 10\log\left(\frac{4\pi df}{c}\right)^2 = 10\log(32\pi d)^2 = 10\log(10,000) = 40 \text{ dB}$$

In a near-field region where magnetic fields are relatively strong, power transferred via a non-radiative mechanism, such as by a magnetic field of an inductive coil, may dissipate with distance. Further, power transfer via non-radiative mechanisms that rely on near-field interactions may react to receive structures and electromagnetic absorption in the vicinity. Magnetic fields used by an inductive coil may have a power transfer efficiency that is inversely proportional to the third power of the distance between the inductive coil and the patient. In contrast, power transfer by far field interactions is inversely proportional to the square of the distance between a far field transmitter and a patient. Therefore, far field power transfer enables greater efficiency of transfer of power across a far field region such that a transmitter structure or power output from the transmitter structure are not affected by a receive structure and its electromagnetic absorption.

Additionally, the implantable medical device 106 may be implanted under several centimeters of tissue of the patient, which may further attenuate the far field radiative signals 104. For example, when the implantable medical device 106 is implanted under one inch of fat, attenuation and impedance mismatch may result in approximately 6 dB of power loss. Thus, as the tissue losses become greater, the power received at the antenna decreases significantly.

Additionally, components of the implantable medical device 106 may further reduce power received via the far field radiative signals 104 that is available to provide therapeutic stimulation. For example, losses at the antenna may be expected to reduce the power by about 5-10 dB, and losses at a rectifier may be expected to reduce the power by about 10-20 dB. Efficient design of the components of the implantable medical device 106 may enable use of the far field radiative signals 104 to provide power for therapeutic stimulation. For example, as explained further below, efficiency of the antenna and the matching network may be increased by using accurate human body simulation models, RF phantoms, or animal or human models (ex vivo and/or in vivo) to test various proposed designs. In another example, efficiency of the rectifier may be increased by sending the far field radiative signals 104 as pulsed signals, by using Schottky diodes, or both.

The implantable medical device 106 may include one or more voltage rectifiers to rectify the far field radiative signals 104 to generate a rectified voltage. The implantable medical device 106 may include one or more voltage multipliers configured to multiply the far field radiative signals 104 received by the antenna 110 to provide a multiplied voltage signal. In the embodiment illustrated in FIG. 1, the voltage rectifier and the voltage multiplier are illustrated as a single rectifier/multiplier 112 component; however, in other embodiments, the voltage rectifier and the voltage multiplier may be separate components. For example, the voltage rectifier may include, be included within, or be coupled to the voltage multiplier.

In a particular embodiment, the voltage rectifier is a multi-stage rectifier, such as a multi-stage complementary rectifier. The voltage rectifier may include Schottky diodes. In a different implementation, diode functionality can be implemented using complementary metal-oxide-semiconductor (CMOS) devices, such as a transistor having the gate and drain shorted together, a p-n junction diode, or a Schottky diode. Schottky diodes generally have high frequency performance and low forward-bias voltage. For example, the Schottky diodes may have a forward bias voltage of 0.4 volts or less, 0.15 volts or less, or 0.1 volts or less at a frequency of interest (such as a frequency of the far field radiative signals 104). Low forward bias voltage of the voltage rectifier may enable rectification at lower input biases which may be desirable for low power operation. Low forward bias voltage of the voltage rectifier may also improve the efficiency of the power conversion at the implanted medical device as less power will be consumed forward biasing the voltage rectifier.

The charge storage element 114 may be operative to receive rectified voltage, multiplied voltage, or rectified and multiplied voltage and to store charge responsive to the received voltage. The charge storage element 114 may include a capacitor, a capacitor array, a rechargeable battery, a thin film battery, another charge storage element, or a combination thereof. The charge storage element 114 may provide power to other elements of the implantable medical device 106.

The therapy delivery unit 116 may be powered by the charge storage element 114. The therapy delivery unit 116 may be operative to deliver therapy to a target tissue 130 of the patient. For example, therapy delivery unit 116 may include a signal generator that is operative to apply electrical stimulation to the target tissue 130. In another example, the therapy delivery unit 116 is a drug delivery unit that is operative to deliver a drug as the therapy to the patient. The target tissue 130 may include neural tissue (e.g., one or more areas of the brain, the spinal cord, a cranial nerve, or another nerve), muscular tissue (e.g., a heart muscle), or other tissue. In a particular embodiment, the target tissue 130 includes one or more of a vagus nerve, a trigeminal nerve, a glossopharyngeal nerve, and a hypoglossal nerve.

In a particular embodiment, the charge storage element 114 may be sized or configured to store only enough charge to deliver the therapy during a short time period relative to typically implantable medical device batteries. To illustrate, the charge storage element 114 may store enough charge to deliver the therapy during a period of 3 days or less. In another example, the charge storage element 114 may store enough charge to deliver the therapy during a period of 24 hours or less. In other examples, the charge stored by the charge storage element 114 is sufficient to deliver the therapy during a period of 12 hours or less, during a period of 6 hours or less, during a period of 3 hour or less, during a period of 2 hour or less, during a period of 1 hour or less, during a period of 30 minutes or less, during a period of 15 minutes or less, during a period of 10 minutes or less, during a period of 5 minutes or less, during a period of 2 minutes or less, during a period of 1 minutes or less, during a period of 30 seconds or less, or even during a period of 15 seconds or less. In a particular embodiment, the charge storage element 114 stores enough charge to deliver only a single treatment. The single treatment may be a single electrical pulse, or a burst including a plurality of electrical pulses.

Thus, the implantable medical device 106 may be relatively small, since the large high capacity power storage requirement is alleviated. Further, the implantable medical device 106 may be provided power via far field radiative powering, which may increase patient compliance and mobility relative to near-field and/or inductive powering.

FIG. 2 is a block diagram of a second particular embodiment of a system 200 including a second embodiment of an implantable medical device 206. The implantable medical device 206 includes a number of elements in common with the implantable medical device 106 of FIG. 1. For example, in the embodiment illustrated in FIG. 2, the implantable medical device 206 includes the antenna and matching network 110, the voltage rectifier and voltage multiplier 112, the charge storage element 114 and the therapy delivery unit 116, each of which operates as explained with reference to FIG. 1

The implantable medical device 206 may include a DC-to-DC converter 118 coupled to the voltage rectifier, coupled to the voltage multiplier, or coupled to the rectifier/multiplier 112. In one instance, the DC-to-DC converter 118 can be a boost converter used to step-up the voltage. In a further instance, the DC-to-DC converter 118 can be a step-up regulator. The DC-to-DC converter 118 may be configured to receive output of the rectifier, the voltage multiplier, or the rectifier/multiplier 112 to which the DC-to-DC converter 118 is coupled.

The DC-to-DC converter 118 may have a relatively low input resistance and a relatively high output resistance, which may facilitate impedance matching between the antenna and other components of the implantable medical device 206, such as the charge storage element 114. For example, the resistance of the antenna may be relatively low (e.g., from a few ohms up to about 50 ohms). A matching network to match from this low resistance to a very high resistance (e.g., 1000 Ohms) may have large losses. The DC-to-DC converter 118 may bridge the gap between this resistance mismatch by providing a relatively low input resistance but high output resistance with high efficiency (e.g., about 90% or more). For example, the high output resistance may be greater than the low input resistance by at least 40 times, may be greater than the low input resistance by at least 20 times, may be greater than the low input resistance by at least 10 times, may be greater than the low input resistance by at least 6.25 times, may be greater than the low input resistance by at least 4 times, may be greater than the low input resistance by at least 3 times, or may be greater than the low input resistance by at least 2 times. In a particular embodiment, the high output resistance is approximately 666 KOhms and the low input resistance is approximately 107 KOhms.

The DC-to-DC converter 118 may improve efficiency of the implantable medical device 206 relative to a similar implantable medical device that does not include the DC-to-DC converter 118 (such as the implantable medical device 106 of FIG. 1). In particular, the DC-to-DC converter 118 may be used to generate sufficient voltage to bias other components of the implantable medical device 206 (e.g., CMOS circuits) with a relatively low input voltage requirement. For example, at least one of the voltage multiplier, the charge storage element 114, the therapy delivery unit 116, a control unit (such as a control unit 320 of FIG. 4), and the voltage rectifier may be a CMOS circuit, and the DC-to-DC converter 118 may be configured to generate voltages operative to bias the subsequent CMOS circuit or circuits.

FIG. 3 is a block diagram of a third particular embodiment of a system 300 including a third embodiment of an implantable medical device 306. The implantable medical device 306 includes a number of elements in common with the implantable medical device 206 of FIG. 2. For example, in the embodiment illustrated in FIG. 3, the implantable medical device 306 includes the antenna and matching network 110, the voltage rectifier and voltage multiplier 112, the DC-to-DC converter 118, the charge storage element 114 and the therapy delivery unit 116, each of which operates as explained with reference to FIGS. 1 and 2.

In the implantable medical device 306, the therapy delivery unit 116 is a signal generator 316. The signal generator 316 may be operative to be electrically coupled to one or more electrodes 318. The electrode(s) 318 may be configured to be positioned in proximity to, or attached to, the target tissue 130 of the patient to provide electrical stimulation to the target tissue 130. The electrodes(s) 318 may be coupled directly to the implantable medical device 106 (i.e., without leads) or may be coupled to the implantable medical device 106 via one or more leads (not shown).

In an illustrative example, the implantable medical device 306 may be directly coupled to electrode(s) 318. For example, the electrode(s) 318 may be proximity electrodes that are adapted to be implantable proximate to a portion of the target tissue 130. The implantable medical device 306 may be configured as or may be coupled to a nerve wrap 332 that includes or is coupled to the electrodes 318. For example, components of the implantable medical device 306 (e.g., the antenna and matching network 110, the voltage rectifier and voltage multiplier 112, the DC-to-DC converter 118, the charge storage element 114, the signal generator 316, other components, or a combination thereof) may be coupled to a flexible circuit board 334, which may be embedded within or coupled to the nerve wrap 332. The proximity electrodes may be provided on a portion of the nerve wrap 332 that is configured to make contact with the target tissue 130. For example, the proximity electrodes may be printed on or otherwise applied to a portion of the nerve wrap 332 or the flexible circuit board 334. In other embodiments, the implantable medical device 306 has a metal case (not shown) or another biologically compatible housing that at least partially contains components of the implantable medical device 306, such as the antenna and matching network 110, the voltage rectifier and voltage multiplier 112, the DC-to-DC converter 118, the charge storage element 114, the therapy delivery unit 116, the signal generator 316, other components, or a combination thereof. When the implantable medical device 306 has a metal case, the metal case may act as one of the electrodes 318.

The signal generator 316 may be adapted to apply electrical stimulation to the target tissue 130. For example, when the target tissue 130 is nerve tissue, the electrical stimulation may induce efferent action potentials, induce afferent action potentials, inhibit intrinsic action potentials, or a combination thereof. In another example, when the target tissue 130 is muscle tissue, the electrical stimulation may cause muscle contraction or may facilitate regulation of muscle contraction.

FIG. 4 is a block diagram of a fourth particular embodiment of a system 400 including a fourth embodiment of an implantable medical device 406. The implantable medical device 406 includes a number of elements in common with the implantable medical device 306 of FIG. 3. For example, in the embodiment illustrated in FIG. 4, the implantable medical device 406 includes the antenna and matching network 110, the voltage rectifier and voltage multiplier 112, the DC-to-DC converter 118, the charge storage element 114 and the signal generator 316, each of which operates as explained with reference to FIGS. 1-3. Although not specifically identified in FIG. 4, components of the implantable medical device 406 may be coupled to or formed on a flexible circuit board, such as the flexible circuit board 334 of FIG. 3. Additionally or in the alternative, the implantable medical device 406 may include, be coupled to or be embedded within a nerve wrap, such as the nerve wrap 332 of FIG. 3. Alternately, the implantable medical device 406 may have a case (not shown) formed of a metal or another biologically compatible material. Further, the implantable medical device 406 may include or be coupled to the electrodes 318, which operate as explained with reference to FIG. 3.

The implantable medical device 406 may include a control unit 320. The control unit 320 may be powered by the charge storage element 114. The control unit 320 may be operative to control delivery of the therapy by a therapy delivery unit, such as the therapy delivery unit 116 of FIGS. 1 and 2 or the signal generator 316 of FIGS. 3 and 4. For example, the control unit 320 may control parameters of therapeutic stimulation provided by the signal generator 316 to the target tissue 130. The parameters of the therapeutic stimulation may include a frequency of therapy delivery (i.e., a time period between treatments), a duty cycle of therapy delivery, a magnitude of therapy delivery (e.g., an amount of energy delivered to the target tissue 130 during a treatment, a magnitude of a voltage of an electrical signal used to deliver the therapy, a magnitude of a current of the electrical signal, or a combination thereof), and a mode of therapy delivery (e.g., a single pulse mode or a burst mode including a plurality of pulses). Other parameters may also be controlled by the control unit 320, such as a location treated when more than one target tissue 130 can be selected for treatment; whether the treatment includes electrical stimulation, delivery of a drug, other treatment, or a combination thereof; and whether electrical signals applied to the target tissue 130 induce efferent signals, induce afferent signals, bias the target tissue to near a firing threshold, inhibit intrinsic efferent or afferent signals, and so forth.

In a particular embodiment, the control unit 320 may cause the therapeutic stimulation to be applied to the target tissue 130 responsive to a sensed patient parameter (e.g., a condition, state or value associated with the body of the patient).

For example, the control unit 320 may receive information via one or more of the electrodes 318 or from another sensor (not shown), and may control application of therapeutic stimulation based on the received information. Therapeutic stimulation that is based on or responsive to the sensed patient parameter may include "active," "responsive," "closed-loop," "feedback," or "triggered" stimulation.

In another embodiment, the control unit 320 may cause the therapeutic stimulation to be applied to the target tissue 130 without sensing or detecting a patient parameter. For example, the control unit 320 may cause the signal generator 316 to apply a series of electrical pulses to the target tissue 130 periodically, intermittently, or continuously throughout the day, or according to another predetermined schedule (e.g., a circadian schedule or another predetermined treatment cycle). This type of stimulation may include "passive," "periodic," "continuous," "open-loop," "non-feedback," or "prophylactic" stimulation.

In another embodiment, the control unit 320 may cause the therapeutic stimulation to be applied to the target tissue 130 responsive to the far field radiative signals 104 or wireless control signals. For example, the control unit 320 may cause the signal generator 316 to apply a series of electrical pulses to the target tissue 130 according to a predetermined schedule during or after receipt of the far field radiative signals 104 or wireless control signals. To illustrate, when the far field radiative signals 104 or wireless control signals are received, receipt of the far field radiative signals 104 or wireless control signals may cause the control unit 320 to initiate therapeutic stimulation without delay or according to a predetermined delay. This type of stimulation may be referred to as "externally controlled" stimulation. In the case that the far-field radiative signals 104 are used to wirelessly deliver power to the implantable medical device 406, the implantable medical device 406 may deliver therapy when a sufficient power supply is received.

In another embodiment, the control unit 320 may use a combination of active, passive and externally controlled stimulation. For example, in response to receipt of the far field radiative signals 104, the control unit 320 may initiate stimulation responsive to a sensed patient parameter (e.g., sensing one or more patient parameters and applying stimulation responsive to the one or more sensed patient parameters).

FIG. 5 is a block diagram of a fifth particular embodiment of a system 500 including a fifth embodiment of an implantable medical device 506. The implantable medical device 506 includes a number of elements in common with the implantable medical device 406 of FIG. 4. For example, in the embodiment illustrated in FIG. 5, the implantable medical device 506 includes the antenna and matching network 110, the voltage rectifier and voltage multiplier 112, the step-up regulator 118, the charge storage element 114, the signal generator 316, and the control unit 320, each of which operates as explained with reference to one or more of FIGS. 1-4. Although not specifically identified in FIG. 5, components of the implantable medical device 506 may be coupled to or formed on a flexible circuit board, such as the flexible circuit board 334 of FIG. 3. Additionally or in the alternative, the implantable medical device 506 may include, be coupled to or be embedded within a nerve wrap, such as the nerve wrap 332 of FIG. 3. Alternately, the implantable medical device 506 may have a case (not shown) formed of a metal or another biologically compatible material. Further, the implantable medical device 506 may include or be coupled to the electrodes 318, which operate as explained with reference to FIG. 3.

The implantable medical device 506 may include a threshold detector 322 coupled to the charge storage element 114. The threshold detector 322 may be configured to determine when charge stored at the charge storage element 114 satisfies a charge threshold. The threshold detector 322 may provide an indication to the control unit 320 when the charge threshold is satisfied. The control unit 320 may control delivery of the therapy by the therapy delivery unit (e.g., the signal generator 316) responsive to the indication from the threshold detector 322. For example, the control unit 320 may cause the signal generator 316 to deliver the therapy responsive to receiving an indication that the charge threshold is satisfied.

The charge threshold may be set based on a power requirement of the implantable medical device 506 to deliver the therapeutic stimulation. In a particular embodiment, the charge threshold may be set according to an amount of charge needed to deliver one treatment (i.e., a single dose or instance of therapeutic stimulation) to the target tissue 130. In a particular embodiment, the implantable medical device 506 has a power requirement of 100 microwatts or less to deliver one treatment (i.e., a single dose or instance of therapeutic stimulation). The implantable medical device 506 may have a power requirement of 50 microwatts or less, 20 microwatts or less, or 10 microwatts or less to deliver one treatment. The charge threshold may be satisfied when the charge storage element 114 has sufficient charge to meet the power requirement for a predetermined number of treatments (e.g., a single treatment).

In an embodiment, a duty cycle of the therapy may be controlled by a duty cycle of power delivery from the external power source (e.g., the far field transmitter 102). For example, the far field transmitter 102 may periodically or occasionally transfer power wirelessly to the implantable medical device 506 according to a duty cycle associated with the far field transmitter 102. At least a portion of the power may be stored by the charge storage element 114. The threshold detector 322 may determine when the charge storage element 114 has obtained sufficient charge to satisfy the charge threshold. In response to the charge threshold being satisfied, the control unit 320 may cause energy to be delivered through the therapy delivery unit 116 (or the signal generator 316) to deliver therapy to the target tissue 130.

In another embodiment, the charge threshold may be set according to an amount of charge needed to deliver more than one treatment, such as a number of treatments specified for a particular amount of time, such as at least 3 days, at least 1 day, at least 12 hours, at least 6 hours, at least 3 hours, at least 2 hours, at least 1 hour, at least 30 minutes, at least 15 minutes, at least 10 minutes, at least 5 minutes, at least 2 minutes, at least 1 minute, at least 30 seconds, at least 15 seconds, at least 10 seconds, or less than 10 seconds. In this embodiment, the implantable medical device 506 may include control logic, such as the control unit 320, that controls application of the therapy. For example, the control unit 320 may control parameters of the therapy such as timing, duty cycle, current amplitude, voltage amplitude, and frequency of signals applied to the target tissue 130.

In a particular embodiment, the control unit 320 may be programmable while the implantable medical device 506 is implanted in a patient. For example, the implantable medical device 506 may include a receiver 530 coupled to the antenna. The receiver 530 may also be coupled to the control unit 320, the threshold detector 322, or both. The receiver 530 may be configured to receive therapy parameter data from an external source. For example, the therapy parameter data may be received via modulation of the far field radiative signals 104 from the far field transmitter 102. The therapy parameter data may specify parameters of the therapy to be delivered to the patient. The receiver 530 may provide the received therapy parameter data to the control unit 320 or to the threshold detector 322 to program the parameters of the therapy to be delivered to the patient. The therapy parameter data may specify, for example, a frequency of therapy delivery, a duty cycle of therapy delivery, a magnitude of therapy delivery, a mode of therapy delivery, or a combination thereof. Available modes of therapy delivery may include a single pulse mode and a burst mode. In the burst mode, the therapy is delivered via one or more bursts, where each burst includes a plurality of pulses. Alternately or in addition, the therapy parameter data may specify a charge threshold to be applied by the threshold detector. For example, to modify an amount of energy to be applied by the signal generator 316 to the target tissue 130 during a single treatment, the charge threshold may be modified such that the modified charge threshold is satisfied when the charge storage element 114 stores sufficient charge to provide the single treatment.

In a particular embodiment, the implantable medical device 506 may use backscatter to transmit data to the far field transmitter 102 or another device. For example, the implantable medical device 506 may modulate backscattered energy in a manner that may be detected by a device external to the patient, such as the far field transmitter 102. In a particular embodiment, such as when the far field transmitter 102 continuously provides power to the implantable medical device 506, third order backscatter may be used to send information from the implantable medical device 506 to an external device. For third order backscatter, nonlinear components of the implantable medical device 506 may be used to generate a third order frequency harmonic component when exposed to energy of a particular frequency. For example, one or more diodes may be used as non-linear components. In this example, the diodes may be separate components or diodes of the voltage rectifier/multiplier 112 may be used to generate the third order frequency harmonic component. The third order frequency harmonic components may be modulated or enhanced to enable generation of a frequency component that is far removed from a fundamental frequency of the far field radiative signal 104. For example, a high-Q resonant circuit which is resonant around the third order frequency can be used to enhance the generation of this third order frequency harmonic component from the non-linear component. In another implementation, a high-frequency/radio-frequency amplifier, that maybe narrowband around the third order frequency harmonic component, can be used alone or in conjunction with the tuned high-Q resonant circuit, to enhance and amplify the third order frequency harmonic component. Thus, an external receiver (of the far field transmitter 102 or of another device external to the patient) may be able to tune to the third order frequency component without being saturated by the fundamental frequency, because the third order frequency component is sufficiently removed from the fundamental frequency so that power transmission and data transmission can occur at the same time (e.g., without time division duplexing the power transmission and data transmission). Because nonlinear components of the implantable medical device 506 naturally generate third order harmonics, modulation of such components to send information from the implantable medical device 506 to the external device may use little or no additional power.

Figure 6:
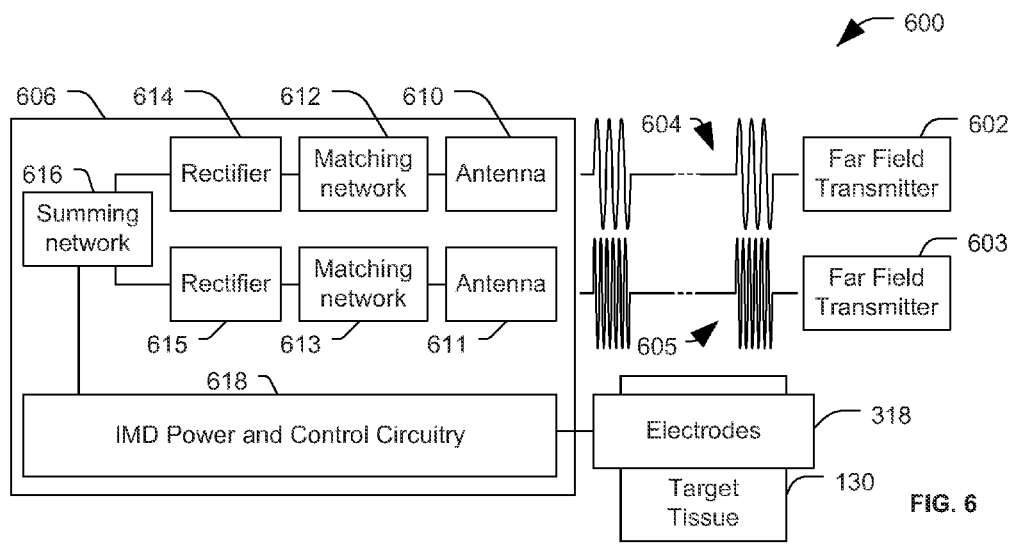
FIG. 6 is a block diagram of a sixth particular embodiment of a system including an implantable medical device and a far field transmitter.
Figure 7:
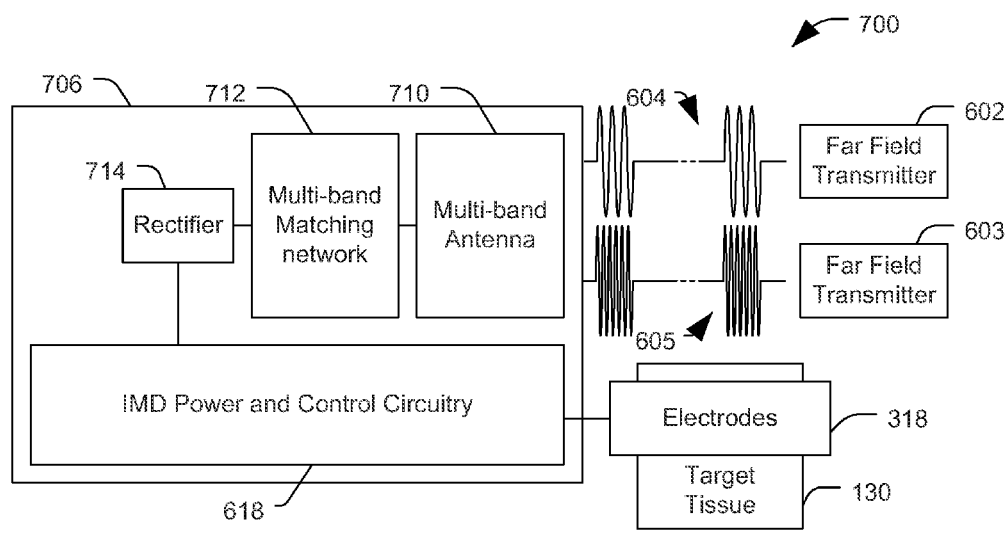
FIG. 7 is a block diagram of a seventh particular embodiment of a system including an implantable medical device and a far field transmitter.

FIGS. 6 and 7 illustrate embodiments in which an implantable medical device is supplied with at least a portion of its operating power simultaneously or concurrently from two or more far field transmitters. For example, a first far field transmitter 602 may provide power to the implantable medical device via first far field radiative signals 604 in a first frequency band, and a second far field transmitter 603 may simultaneously or concurrently provide power to the implantable medical device via second far field radiative signals 605 in a second frequency band.

Referring to FIG. 6, a block diagram of a sixth particular embodiment of a system 600 including a sixth embodiment of an implantable medical device 606 is shown. The implantable medical device 606 includes multiple antennas, including a first antenna 610, a second antenna 611, and possibly one or more additional antennas (not shown). The implantable medical device 606 may also include one or more matching networks associated with one or more of the antennas, such as a first matching network 612 associated with the first antenna 610, a second matching network 613 associated with the second antenna 611, and possibly one or more additional matching networks (not shown) associated with other antennas (not shown).

In a particular embodiment, each antenna 610, 611 and/or each matching network 612, 613 may be configured or tuned to operate at a particular frequency or frequency band. For example, the first antenna 610 and/or the first matching network 612 may be configured or tuned to receive far field radiative signals in a first frequency band that includes a frequency of the first far field radiative signals 604. The second antenna 611 and/or the second matching network 613 may be configured or tuned to receive far field radiative signals in a second frequency band that includes a frequency of the second far field radiative signals 605. For example, the first and second frequency bands may be centered at one of approximately 433 MHz and 900 MHz, respectively, approximately 433 MHz and 2.4 GHz, respectively, approximately 433 MHz and 5.8 GHz, respectively, approximately 900 MHz and 2.4 GHz, respectively, approximately 900 MHz and 5.8 GHz, respectively, and approximately 2.4 GHz and 5.8 GHz, respectively. The first far field radiative signals 604 and the second far field radiative signals 605 may include at least a portion of the signals that are transmitted concurrently, or may be transmitted in an interleaved fashion. When other antennas or matching networks are present, these may be configured or tuned to receive far field radiative signals in the first frequency band, in the second frequency band, in another first frequency band, or in a combination thereof. Thus, when exposure limits or other radiofrequency transmission limitations (e.g., FCC and/or FDA regulations) limit transmission power at a particular frequency, more than one frequency may be used for far field radiative power transfer.

The implantable medical device 606 may also include one or more rectifiers. Each rectifier may be associated with a particular antenna. For example, a first rectifier 614 may be associate with the first antenna 610 and the first matching network 612, a second rectifier 615 may be associate with the second antenna 611 and the second matching network 613, and possibly one or more additional rectifiers (not shown) may be associate with other antennas and matching networks (not shown). In another configuration, one rectifier, such as the first rectifier 614, may be associated with multiple antennas. For example, the first rectifier 614 may be coupled to a set of antenna (of which the first antenna 610 is a representative antenna) that are each configured or tuned to receive the first far field radiative signals 604, and the second rectifier 615 may be coupled to a set of antenna (of which the second antenna 611 is a representative antenna) that are each configured or tuned to receive the second far field radiative signals 605.

When the implantable medical device 606 includes multiple rectifiers, such as the first rectifier 614 and the second rectifier 615, the rectifiers 614, 615 may be coupled to a summing network 616. The summing network 616 may combine the direct current (DC) output of the rectifiers 614, 615 and provide the combined DC output to other power and/or control circuitry, represented in FIG. 6 as implantable medical device (IMD) power and control circuitry 618.

The IMD power and control circuitry 618 may include any combination of power modification, power storage, IMD control, therapy and sensing circuitry as described above with reference to FIGS. 1-5 or as described subsequently with reference to FIGS. 7 and 8. For example, the IMD power and control circuitry 618 may include a voltage multiplier (or the rectifiers may be rectifier/multiplier units as described with reference to FIGS. 1-5), a DC-to-DC converter (such as the DC-to-DC converter 118 of FIGS. 2-5), a charge storage element (such as the charge storage element 114 of FIGS. 1-5), a therapy delivery unit (such as the therapy delivery unit 116 of FIGS. 1 and 2), a signal generator (such as the signal generator 316 of FIGS. 3-5), a control unit (such as the control unit 320 of FIGS. 4 and 5), a threshold detector (such as the threshold detector 322 of FIG. 5), sensor circuitry (such as sensor circuitry 816 of FIG. 8), other components, or a combination thereof. Although not specifically identified in FIG. 6, components of the implantable medical device 606 may be coupled to or formed on a flexible circuit board, such as the flexible circuit board 334 of FIG. 3. Additionally or in the alternative, the implantable medical device 606 may include, be coupled to or be embedded within a nerve wrap, such as the nerve wrap 332 of FIG. 3. Alternately, the implantable medical device 606 may have a case (not shown) formed of a metal or another biologically compatible material. Further, the implantable medical device 606 may include or be coupled to the electrodes 318, which operate as explained with reference to FIG. 3.

The implantable medical device 606 may also include one or more receivers (not shown in FIG. 6), such as the receiver 530 of FIG. 5. For example, the implantable medical device 606 may include a single receiver coupled to one or more of the antennas 610, 611. To illustrate, a first receiver may be coupled to the first antenna 610, or the first receiver may be coupled to the first antenna 610, to the second antenna 611, and possibly to one or more additional antennas, when additional antennas are present. In this illustrative example, the first receiver may be a multiband receiver capable of receiving data transmitted in several frequency bands. Alternately, the first receiver may be tunable such that the first receiver can receive data via one frequency band at a time and can be adjusted or tuned (e.g., by a control unit) to select a particular frequency band. In another example, the implantable medical device 606 may include multiple receivers. To illustrate, a first receiver may be coupled to the first antenna 610 and a second receiver may be coupled to the second antenna 611. In this illustrative example, the first receiver may be configured to or tuned to receive data via a first frequency band corresponding to the frequency of the first far field radiative signals 604, and a second receiver may be configured to or tuned to receive data via a second frequency band corresponding to the frequency of the second far field radiative signals 605.

Referring to FIG. 7, a block diagram of a seventh particular embodiment of a system 700 including a seventh embodiment of an implantable medical device 706 is shown. The implantable medical device 706 includes one or more multi-band antennas, such as a multi-band antenna 710. The implantable medical device 706 may also include one or more multi-band matching networks with the multi-band antennas 712, such as a multi-band matching network 712. The multi-band antenna 710 and/or the multi-band matching network 712 may be configured or tuned to operate at multiple frequencies or frequency bands. For example, the multi-band antenna 710 and/or the multi-band matching network 712 may be configured or tuned to receive far field radiative signals in a first frequency band that includes the frequency of the first far field radiative signals 604 and in a second frequency band that includes the frequency of the second far field radiative signals 605. For example, the first and second frequency bands may be centered at one of approximately 433 MHz and 900 MHz, respectively, approximately 433 MHz and 2.4 GHz, respectively, approximately 433 MHz and 5.8 GHz, respectively, approximately 900 MHz and 2.4 GHz, respectively, approximately 900 MHz and 5.8 GHz, respectively, and approximately 2.4 GHz and 5.8 GHz, respectively. The first far field radiative signals 604 and the second far field radiative signals 605 may include at least a portion of the signals that are transmitted concurrently, or may be transmitted in an interleaved fashion. Thus, when exposure limits or other radiofrequency transmission limitations (e.g., FCC regulations) limit transmission power at a particular frequency, more than one frequency may be used for far field radiative power transfer.

The implantable medical device 706 may also include one or more rectifiers, such as a rectifier 714 coupled to the multi-band antenna 710 and the multi-band matching network 712. Direct current (DC) output of the rectifier 714 may be provided to the implantable medical device (IMD) power and control circuitry 618. As explained above, the IMD power and control circuitry 618 may include any combination of power modification, power storage, IMD control, therapy and sensing circuitry as described above with reference to FIGS. 1-6 or as described subsequently with reference to FIG. 8. The implantable medical device 706 may include, be coupled to or be embedded within a nerve wrap, such as the nerve wrap 332 of FIG. 3. Alternately, the implantable medical device 706 may have a case (not shown) formed of a metal or another biologically compatible material. Further, the implantable medical device 706 may include or be coupled to the electrodes 318, which operate as explained with reference to FIG. 3.

The implantable medical device 706 may also include one or more receivers (not shown in FIG. 7), such as the receiver 530 of FIG. 5. For example, the implantable medical device 706 may include a multi-band receiver capable of receiving data transmitted in several frequency bands coupled to the multi-band antenna 710. Alternately, the receiver may be tunable such that the receiver can receive data via one frequency band at a time and can be adjusted or tuned (e.g., by a control unit) to select a particular frequency band. In another example, the implantable medical device 706 may include multiple receivers. To illustrate, a first receiver and a second receiver may be coupled to the multi-band antenna 710. The first receiver may be configured to or tuned to receive data via a first frequency band corresponding to the frequency of the first far field radiative signals 604, and a second receiver may be configured to or tuned to receive data via a second frequency band corresponding to the frequency of the second far field radiative signals 605.

Thus, the implantable medical devices 606 and 706 are capable of receiving far field radiative signals from multiple far field transmitters 602, 604. The far field radiative signals 604, 065 may be in the same frequency band, in different bands, or in overlapping frequency bands. Using multiple antennas may enable increased power reception. Using multiple frequency bands may enable increased power transfer. For example, providing antennas configured to receive two or more different frequency bands may allow an increase in overall transmission power to the implantable medical devices 606, 706 since a transmission power restriction may apply to each band separately. To illustrate, when each frequency band is limited to 1 watt of transmission power, two frequency bands may be used to transmit approximately 2 watts of power.

FIG. 8 is a block diagram of an eighth particular embodiment of a system 800 including an implantable medical device 806 and one or more far field transmitter 802. The far field transmitters 802 and antenna(s) 810 may include any combination of transmitters and antennas described above with reference to FIGS. 1-7. For example, a single far field transmitter and a single antenna may be used. In another example, multiple far field transmitters may be used with a single antenna. In yet another example, multiple far field transmitters may be used with a multiple antennas. In still another example, a single far field transmitter may be used with a multiple antennas. The antenna(s) 810 may be coupled to or may include one or more matching networks (not shown). Additionally, the antenna(s) 810 may be coupled to one or more rectifiers 814 that provide a DC output to the IMD power and control circuitry 618.

The implantable medical device 806 also includes sensor circuitry 816. The sensing circuitry 816 may be powered by a charge storage element of the IMD power and control circuitry 618. The sensor circuitry 816 may be configured to receive a stimulus and to generate a digital or analog output corresponding to the stimulus. The stimulus may be electrical, optical, magnetic, chemical or physical. For example, the stimulus may correspond to or be indicative of presence or concentration of a chemical, such as a chemical that occurs naturally within a patient's body (e.g., a neurotransmitter, a hormone, blood oxygen, a metabolic product, etc.) or a foreign chemical (e.g., a medication). In another example, the stimulus may correspond to or be indicative of presence or other characteristics of an electrical signal, such as a naturally occurring electrical signal (e.g., an endogenous action potential) or an induced electrical signal (e.g., an induced action potential). In yet another example, the stimulus may correspond to or be indicative of presence or other characteristics of a physical function or parameter, such as a movement of the body or a portion of the body, respiratory rate, pulse rate, blood pressure, body temperature, etc.

The output of the sensor circuitry 816 may be provided to the IMD power and control circuitry 618. The IMD power and control circuitry 618 may use the output as feedback related to a therapy provided by the implantable medical device 806. For example, when the implantable medical device 806 applies stimulation or another therapy to the target tissue 130, electrodes 818 may be used to detect the stimulus or a body response to the stimulus and to send information to the sensor circuitry 816. The sensor circuitry 816 may send the output to the IMD power and control circuitry 618, and the IMD power and control circuitry 618 may adjust the stimulation or other therapy based on a value of the output.

In a particular embodiment, information descriptive of the output of the sensor circuitry 816, such as a logical or numeric value, may be transmitted by the implantable medical device 806 to an external device. For example, the IMD power and control circuitry 618 may process the output of the sensor circuitry 816 to determine information that is to be transmitted to the external device. One or more non-linear components of the IMD power and control circuitry 618 may be used to modulate backscatter of the far field radiative signals 804 to transmit the information to the external device, as described with reference to FIG. 5.

In a particular embodiment, the implantable medical device 806 does not include a therapy delivery unit and is only used to gather and transmit sensed data from the patient's body. Thus, the far field radiative signals 802 may be used to power an implantable medical device that is a sensor or is primarily used as a sensor.

In addition to the specific embodiments illustrated in FIGS. 1-8, other embodiments and variations are envisioned. For example, components of any of the implantable medical devices 106, 206, 306, 406, 506, 606, 706, and 806 may be coupled to or formed on a flexible circuit board, such as the flexible circuit board 334 of FIG. 3. To illustrate, one or more antennas, one or more matching networks, one or more voltage multipliers, one or more rectifiers, one or more DC-to-DC converters, one or more charge storage elements, one or more therapy delivery units, one or more control units, one or more signal generators, one or more receivers, one or more threshold detector, sensor circuitry, or a combination thereof, may be integrated on the flexible circuit board 334.

Additionally or in the alternative, any of the implantable medical devices 106, 206, 306, 406, 506, 606, 706, and 806 may include, be coupled to or be embedded or housed within an enclosure 532 of FIG. 5. The enclosure 532 may be flexible, such as the nerve wrap 332 of FIG. 3, or may be a substantially rigid, hermetically sealed case. The enclosure 532 may house or partially house one or more of the other components, such as one or more antennas, one or more matching networks, one or more receivers, one or more rectifiers, one or more voltage multipliers, one or more DC-to-DC converters, one or more charge storage elements, one or more threshold detectors, one or more control units, one or more signal generators, one or more therapy delivery units, sensor circuitry, or a combination thereof. To improve power transfer to the implantable medical device 106, 206, 306, 406, 506, 606, 706, or 806, the enclosure 532 may be formed at least partially of a radiofrequency (RF) transparent material. The RF transparent material may be selected to not attenuate or degrade high-frequency signals, such as the far field radiative signals 104. Further, the RF transparent material may be selected to be biocompatible and hermetically sealable. Examples of suitable materials include ceramics (such as, low-temperature co-fired ceramic (LTCC), alumina, etc.), liquid crystal polymers, polyimides, plastics, and polyether-based thermoplastic polyurethanes (TPU) (e.g., Tecothane® TPU).

In a particular embodiment, the enclosure 532 may be formed of a material that has a permittivity value that results in a small, reduced or minimal impedance boundary reflection loss between the enclosure 532 and a tissue layer of the patient. In a particular embodiment, the enclosure 532 may be formed of a material that is selected such that, as a whole, electric properties of the material (e.g., conductivity, permittivity, permeability) reduce or minimize total power losses due to all effects, including attenuation, dielectric/impedance boundary reflections, dielectric resonance, eddy currents, and so forth.

In a particular embodiment, dimensions of the enclosure 532 (e.g., length, width, and/or thickness) may be selected to provide efficient power transfer. For example, the dimensions of the enclosure 532 may be selected to enable use of an efficient antenna design. To illustrate, the enclosure 532 may have a length or area of at least one side that is selected to be coupled to or to house an antenna with a length or area that enables acceptable antenna gain while maintaining flexibility for placement of the implantable medical device 106, 206, 306, 406, 506, 606, 706, 806.

An implantation location of the implantable medical device 106, 206, 306, 406, 506, 606, 706, 806 may be selected based at least in part on providing efficient power transfer. For example, a shallower implantation depth may result in less tissue absorption based attenuation, thereby providing improved energy transfer efficiency relative to a deeper implantation depth. Dielectric properties of specific tissues that will surround the implantable medical device 106, 206, 306, 406, 506, 606, 706, 806 may also be considered. For example, higher permittivity of the specific tissues may result in higher gains for electrically-small antennas but greater tissue absorption of the electromagnetic waves, and lower conductivity may result in less tissue absorption of the electromagnetic waves.

In addition to being designed for efficient power transfer, the implantable medical device 106, 206, 306, 406, 506, 606, 706, 806 may be designed to reduce power consumed to provide therapy. For example, parameters of the therapy may also be controlled (e.g., by the control unit 320) or configured to reduce power consumption. To illustrate, a strength duration curve of nerve fibers to be stimulated may be consider to enable reduced power consumption. The strength duration curve is a relationship between current and pulse width of a therapeutic signal. When applying stimulation to a nerve fiber using the therapeutic signal, as the duration of stimulus decreases, the applied current has to increase to bring the nerve fiber to a threshold potential. The current and pulse width of the therapeutic signal may be selected to efficiently provide energy to the nerve fiber.

The implantable medical device 106, 206, 306, 406, 506, 606, 706, 806 may also or in the alternative reduce power consumption by taking a circadian rhythm of the patient into account. For example, the implantable medical device 106, 206, 306, 406, 506, 606, 706, 806 may provide more frequent, higher duty cycle, higher frequency, and/or higher amplitude stimulations at times when the patient is most likely to have a seizure and a less intense, less frequent, and/or lower power consumption stimulation when the patient is less likely to have a seizure (e.g., based on personal history of the patient).

In another example, the implantable medical device 106, 206, 306, 406, 506, 606, 706, 806 may provide stimulation responsive to a sensed value. For example, a sensor (such as the sensor circuitry 816 or another sensor) may detect a patient parameter associated with the patient and may provide a sensed value to the implantable medical device 106, 206, 306, 406, 506, 606, 706, 806, either directly or via the far field transmitter 102. The patient parameter may include, for example, a parameter associated with a seizure, such as a cardiac-based seizure response, a nerve action potential, or an EEG-based seizure response. Other values may also, or in the alternative, be sensed and stimulation may be provided responsive to the sensed value or values.

In another example, circuits or firmware may be selected or configured to improve efficiency of the implantable medical device 106, 206, 306, 406, 506, 606, 706, 806. To illustrate, the control unit 320 may include a microcontroller. The microcontroller may use a reduced power mode, such as a sleep mode, to reduce power consumption by the control unit 320. For example, the microcontroller may be put in a sleep mode while stimulation is applied to the target tissue 130. To illustrate, the microcontroller may awake (i.e., exit the sleep mode) to initiate application of the stimulation, then return to the sleep mode. The microcontroller may again awake at an end of a stimulation period to end application of the stimulation. As a more specific illustrative example, the threshold detector 322 may be operable to detect an initiate threshold and a cease threshold. The initiate threshold may be satisfied when the charge storage element 114 stores sufficient charge to deliver treatment. The cease threshold corresponds to an amount of power that is sufficient to operate one or more components of the implantable medical device until a next time that power is expected to be received from the far field transmitter. For example, the cease threshold may be set to allow continued operation of one or more sensors or the receiver 530 between on times of the far field radiative signals 104. The cease threshold may be satisfied when charge stored by the charge storage element 114 decreases by a predetermined amount from the initiate threshold or to a predetermined value. In this illustrative example, the microcontroller may awake and initiate application of the stimulation responsive to the threshold detector 322 indicating that the initiate threshold is satisfied. The microcontroller may then sleep until the threshold detector 322 indicates that the cease threshold is satisfied, at which time the microcontroller may awake to end application of the stimulation.

Although only one implantable medical device is shown in each of FIGS. 1-9, a far field transmitter may be used to provide power to more than one implantable medical device at a time. For example, a patient may have two or more implantable medical devices that receive at least a portion of their operating power from the far field transmitter. With inductive power coupling, as opposed to far field radiative power transfer, power coupling is targeted to a relatively small area. Accordingly, it may be difficult or impossible to use inductive coupling to provide power to implantable medical devices at different locations of a patient's body (e.g., one proximate a left vagus nerve and one proximate a right vagus nerve) with a single external inductive powering unit. However, using far field radiative signals enables providing power to such implantable medical devices using a single far field transmitter even though the implantable medical devices are remotely located from one another.

Additionally or in the alternative, a single implantable medical device 106, 206, 306, 406, 506, 606, 706, 806 (and possibly one or more other implantable medical devices) may be supplied with at least a portion of its operating power from two or more far field transmitters 102. For example, a first far field transmitter may supply power to the implantable medical device 106, 206, 306, 406, 506, 606, 706, 806 when the patient is at a first location (e.g., a first room of the patient's home) and a second far field transmitter may supply power to the implantable medical device 106, 206, 306, 406, 506, 606, 706, 806 when the patient is at a second location (e.g., in a second room of the patient's home).

Efficiency of the power transfer may also be improved by designing or tuning the antenna using an accurate 3D high-frequency electromagnetic model and an accurate human RF phantom. For example, a trial-and-error type procedure in which multiple different antenna types and geometries are tested (e.g., a simulation using an optimization search heuristic with the 3D high-frequency electromagnetic model and the human RF phantom) may be used to select a suitable antenna design. Additionally, simulation or physical testing may be used to tune the antenna. For example, resonance frequency seeking may be used to tune a resonant frequency of the antenna to provide efficient power transfer. Further, the antenna and matching network may be actively or passively tuned to provide efficient power transfer. To illustrate, the antenna may be tuned using a varactor that is arranged to change an effective electrical length of the antenna. In another example, a varactor, one or more inductors, one or more capacitors, or a combination thereof may used to tune the matching network.

FIG. 9 is a diagram illustrating a particular embodiment of a system 900 for powering an implantable medical device 906 using a far field transmitter 902. The implantable medical device 906 may correspond to one of the implantable medical devices 106, 206, 306, 406, 506, 606, 706 and 806 of FIGS. 1-8 or one of the additional embodiments or variants explained above. FIG. 9 illustrates particular features of far field radiative signals 904. The far field radiative signals 904 may correspond to one or more of the far field radiative signals 104, 604, 605, and 804 of FIGS. 1-8.

As illustrated in FIG. 9, and as described above, a distance, d, 916 between the far field transmitter 902 and an antenna 908 of the implantable medical device 906 may be greater than twice a wavelength, λ, 918 of the far field radiative signals 904. In the embodiment illustrated in FIG. 9, the far field radiative signals 904 are pulsed. That is, the far field radiative signals 904 have on-times 910 during which electromagnetic waves are generated, and off-times 914 during which no electromagnetic waves are generated. During a particular on-time 910, a burst 912 of energy may be transmitted. As used herein, the frequency of the far field radiative signals 904 refers to a frequency of electromagnetic waves of the burst 912. Relative timing of the on-times 910 and off-times 914 is referred to herein with reference to a duty cycle of the far field radiative signals 904. The pulsed far field radiative signals 904 may have an average transmission power of 1 watt or less. The pulsed far field radiative signals 904 may have a duty cycle of 10% or less, 5% or less, 2% or less, 1% or less, 0.5% or less, 0.266% or less, or 0.2% or less. Each burst 912 of the pulsed far field radiative signals 904 may deliver 100 milliwatts or less of power at the antenna 908. For example, each burst 912 may deliver 50 milliwatts or less, 30 milliwatts or less, 20 milliwatts or less, 10 milliwatts or less, 5 milliwatts or less, or 1 milliwatt or less of power at the antenna 908. During operation, an average input power at the antenna 908 may be 53 microwatts or less and the implantable medical device 906 may have a power conversion efficiency of 11.3 percent or less.

Increasing the power of the far field radiative signals 904 may boost the output voltage, current, and overall efficiency of energy transfer to the implantable medical device 906; however, transmission power at RF frequencies through human tissue is constrained by the exposure limit guidelines for time-varying electromagnetic fields. Pulsing the far field radiative signals 904, as explained above, may achieve a high output voltage and increase the efficiency of components of the implantable medical device 906, such as a voltage rectifier of the implantable medical device 906, while still maintaining a low average power to meet exposure limits, such as the Institute of Electrical and Electronics Engineers (IEEE) C95.1 SAR limits. This pulsing technique may take advantage of a nonlinear increase in voltage rectifier efficiency as relatively large instantaneous powers are used. A width and a frequency of the bursts 912 along with the instantaneous RF power may be selected or adjusted to efficiently and rapidly charge up a charge storage element, such as the charge storage element 114 of FIGS. 1-5 or a charge storage element of the IMD power and control circuitry 618 of FIGS. 6-8. In certain embodiments, one or more components of the implantable medical device 906, such as one or more of a voltage multiplier, a voltage rectifier, a charge storage element, a therapy delivery unit, and a signal generator, is a complementary metal-oxide-semiconductor (CMOS) circuit. In these embodiments, a boost converter or step-up regulator may be configured to generate voltages sufficient to operatively bias the CMOS circuits. For example, a short duty cycle of the far field radiative signals 904, e.g., about 2%, using the pulsed powering technique may enable a CMOS voltage rectifier to generate a sufficient bias with only an average transmit power of 300 mW.

Figure 10:
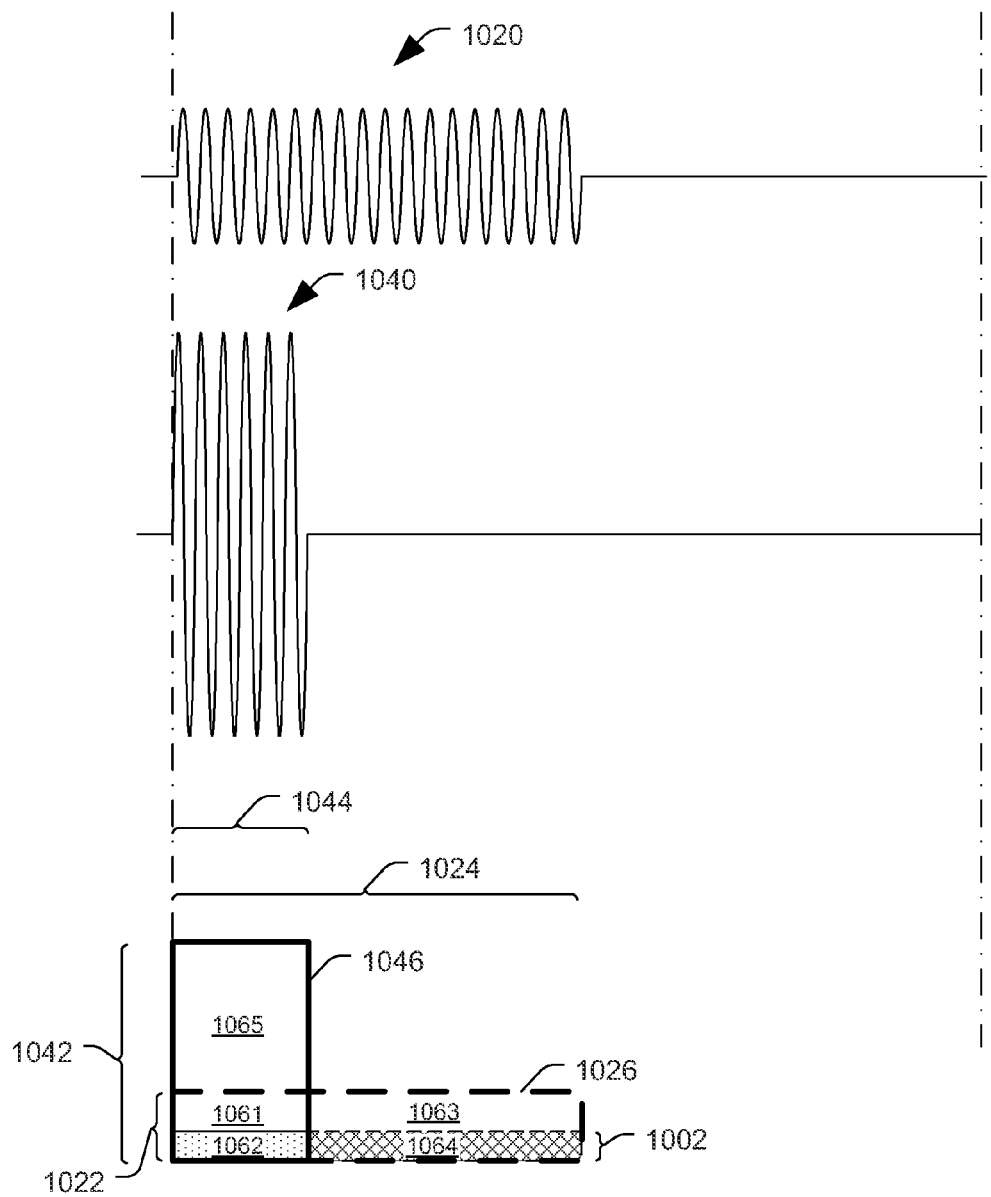
FIG. 10 is a diagram illustrating energy transfer using far field radiative signals with different amplitudes and on-times.

FIG. 10 is a diagram illustrating energy transfer using far field radiative signals with different amplitudes and on-times. In particular, FIG. 10 illustrates a relationship between energy transfer efficiency and a duty cycle of the far field radiative signals. FIG. 10 shows that energy transfer efficiency (and corresponding energy storage efficiency by an implantable medical device) can be improved by using relative high power, short duration transmissions (e.g., short duty cycle), as opposed to lower power, longer duration transmissions (e.g., longer duty cycle).

Two pulses are shown in FIG. 10, including a first pulse 1020 and a second pulse 1040. Each of the pulses 1020 and 1040 represent a far field radiative signal, such as one of the far field radiative signals 104 of FIGS. 1-5, the far field radiative signals 604, 605 of FIGS. 6-7, the far field radiative signals 804 of FIG. 8, or the far field radiative signals 904 of FIG. 9. For purposes of description of FIG. 10, it is assumed that the first pulse 1020 transmits the same total power as the second pulse 1040, and differences in efficiency of reception of the pulses 1020, 1040 are not considered. Thus, the first pulse 1020 provides power that is graphically illustrated by a first area 1026 (enclosed by bold dashed box in FIG. 10, which includes a first portion 1061, a second portion 1062, a third portion 1063 and a fourth portion 1064). Similarly, the second pulse 1040 provides power graphically illustrated by a second area 1046 (enclosed by bold box 1046 in FIG. 10, which includes the first portion 1061, the second portion 1062 and a fifth portion 1065). (Note that in FIG. 10, the power provided by the first pulse 1020 and the power provided by the second pulse 1040 are illustrated overlapping and intersecting one another merely to highlight differences between them. The portions 1061-1065 are used merely for convenience to clarify which portions of FIG. 10 are associated with each pulse 1020, 1040 and do not necessarily correspond to distinct phenomena).

An instantaneous power 1022 of the first pulse 1020 is smaller than an instantaneous power 1042 of the second pulse 1040. Thus, the first pulse 1020 has a longer on-time 1024 than an on-time 1044 of the second pulse 1040 in order to transfer the same amount of energy. That is, a far field radiative signal that uses the first pulse 1020 has a higher duty cycle that a far field radiative signal that uses the second pulse 1040 to transfer the power.

Forward biasing components of the implantable medical device (such as Schottky diodes of a rectifier) requires a threshold voltage and consumes a portion of the voltage, and thus power, transferred to the implantable medical device. For example, while the components are forward biased, instantaneous forward bias power 1002 may be used to provide the forward biasing, and is therefore not available to be stored or used for other purposes. When the second pulse 1040 is used, providing the threshold voltage to forward bias the components may use forward bias power corresponding to the second portion 1062; whereas, when the first pulse 1020 is used, providing the threshold voltage to forward bias the components may use forward bias power corresponding to a sum of the second portion 1062 and the fourth portion 1064. Decreasing the amount of time over which power is received (by using the second pulse 1040 rather than the first pulse 1020) causes the components of the implantable medical device to be forward biased for a shorter time, which provides power savings. Additionally, the instantaneous forward bias power 1002 is a larger percentage of the instantaneous power 1022 of the first pulse 1020 than it is of the instantaneous power 1042 of the second pulse 1040. That is, a larger percentage of the power derived from the first pulse 1020 is used to forward bias the components of the implantable medical device than the percentage of the power derived from the second pulse 1040 that is used to forward bias the components of the implantable medical device. Accordingly, using the second pulse 1040 causes less total power to be consumed for forward biasing components of the implantable medical device. For example, if the power represented in the first area 1026 and the power represented in the second area 1046 are approximately equivalent, then the power gained for storage and use at the implantable medical device by using the second pulse 1040 instead of the first pulse 1020 is approximately equal to the area of the second portion 1062.

Additionally, Shottky diodes are non-linear components that operate more efficiently the further they are forward biased. The non-linear characteristics of Shottky diodes can be described by a relationship of current to forward bias:

$$I \approx I_0 \cdot e^{V_F/(nV_T)}$$

Where I is current that the diode can pass (diode current), $I_0$ is reverse bias saturation current, n is a number that depends on a substrate of the Shottky diodes (e.g., about 1-2 for silicon) and $V_T$ is thermal voltage which is about 26 mV for room temperature, $V_F$ is the forward bias voltage. Thus, as the forward bias voltage, $V_F$, increases, the current that the diode can pass, I, increases exponentially. Considering Ohm's Law, V=IR, or R=V/I, as the voltage increase linearly, the resistance/impedance will decrease exponentially. Thus, the rectifier/multiplier circuit will "impede" the current/power flowing through it less as the forward bias voltage is increased. Stated another way, the diodes behave more like shorts as the forward bias voltage increases, thereby increasing the overall efficiency of the diodes.

Thus, for a particular energy transfer rate, a shorter duty cycle of the far field radiative signals may more efficiently provide power for use and/or storage by the implantable medical device. For example, based on the analysis presented in FIG. 10, and based on in vivo tests that were performed using an ocular implant in an animal subject, a larger portion of total transmitted power may converted to DC current at the implantable medical device when a smaller duty cycle is used. To illustrate, results of the in vivo testing indicated that for a 0.5 W average power transmitted, a 100% duty cycle provided less than 0.10 mW of DC power at the ocular implant. A 50% duty cycle provided more power at the ocular implant than the 100% duty cycle, but still less than 0.10 mW. A 25% duty cycle provided between 0.25 mW and 0.30 mW of DC power at the ocular implant. A 10% duty cycle provided approximately 0.40 mW of DC power at the ocular implant. Finally, a 5% duty cycle provided approximately 0.60 mW of DC power at the ocular implant.

Figure 11:
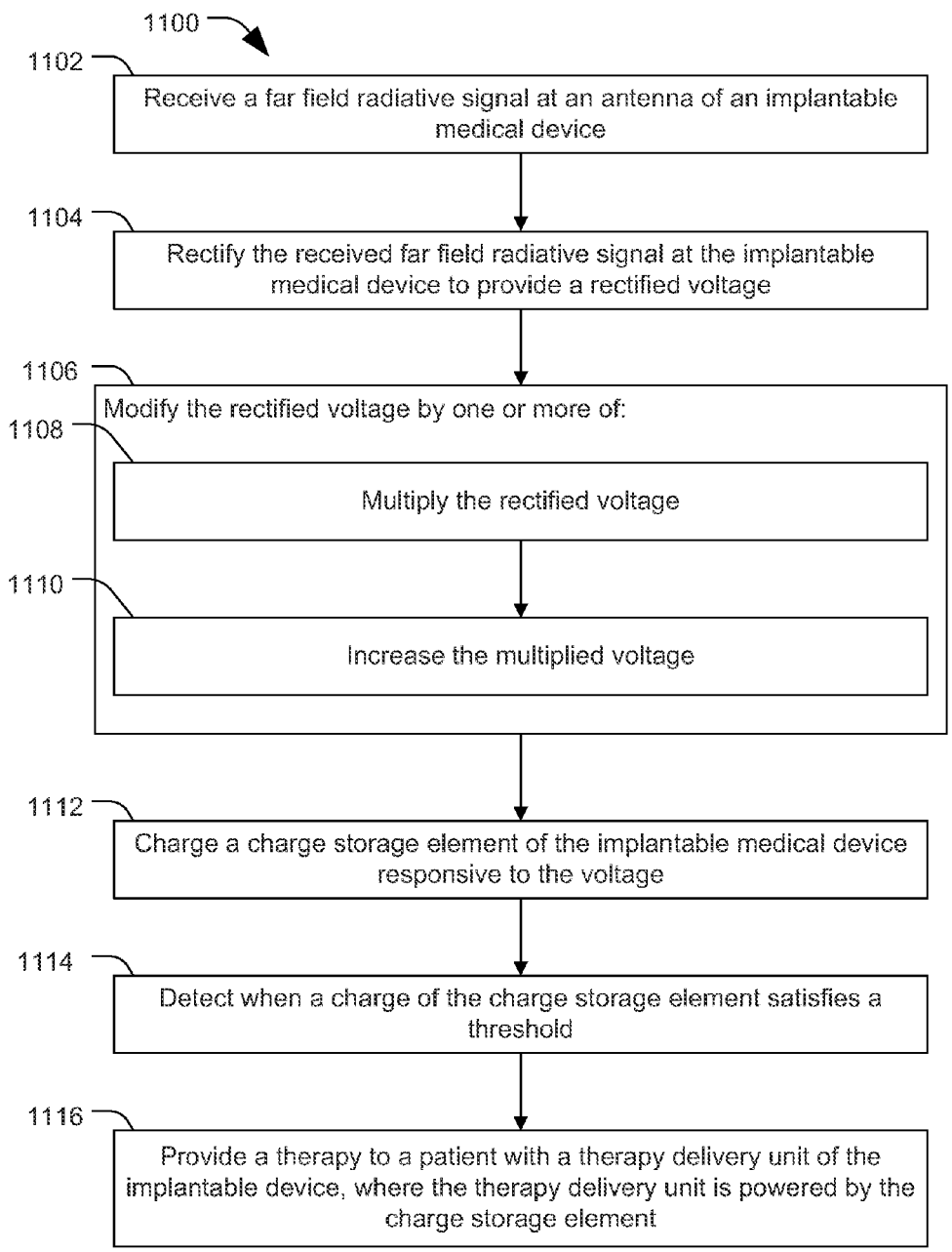
FIG. 11 is flow chart of a particular embodiment of a method of powering an implantable medical device using a far field transmitter.

FIG. 11 is a flow chart of a particular embodiment of a method 1100 of powering an implantable medical device using a far field transmitter. The implantable medical device may correspond to one of the implantable medical devices 106, 206, 306, 406, 506, 606, 706, 806 or 906 of FIGS. 1-9 or one of the additional embodiments or variants described above.

The method 1100 includes, at 1102, receiving a far field radiative signal at an antenna of an implantable medical device. As explained above, a far field radiative signal may include a signal that is transmitted a distance of at least two times a wavelength of the signal. For example, a distance between an antenna of the implantable medical device and a transmitter transmitting the far field radiative signal may be greater than 0.1 meters, greater than 0.15 meters, greater than 0.25 meters, greater than 0.3 meters, greater than 0.5 meters, or greater than 1 meter. The method 1100 may also include, at 1104, rectifying the received far field radiative signal at the implantable medical device to provide a rectified voltage. For example, the rectifier/multiplier 112 may rectify the received far field radiative signal.

The method 1100 may include, at 1106, modifying the rectified voltage. For example, the rectified voltage may be modified, at 1108, by multiplying (i.e., increasing) the rectified voltage (e.g., by the rectifier/multiplier 112 of FIGS. 1-5). In another example, the rectified voltage may be modified, at 1110, by increasing the rectified voltage using a DC-to-DC converter (e.g., a step-up regulator or a boost converter, such as the DC-to-DC converter 118 of FIGS. 1-5). In another example, the rectified voltage may be modified by multiplying the rectified voltage to generate a multiplied voltage and increasing the multiplied voltage using the DC-to-DC converter. In another example, the rectified voltage may be modified by increasing the rectified voltage using DC-to-DC converter to generate an increased voltage and multiplying the increased voltage.

The method 1100 may also include, at 1112, charging a charge storage element (e.g., the charge storage element 112 of FIG. 1-5) of the implantable medical device responsive to the voltage. The method 1100 may also include, at 1114, detecting when a charge of the charge storage element satisfies a threshold. The method 1100 may further include, at 1116, providing a therapy to a patient using a therapy delivery unit of the implantable medical device that is powered by the charge storage element. In a particular embodiment, the therapy is provided responsive to the threshold being satisfied. For example, a control unit (such as the control unit 320 of FIGS. 4 and 5) may be configured to cause the therapy delivery unit to provide the therapy based at least in part on the threshold being satisfied.

Embodiments disclosed herein enable efficiently providing power to an implantable medical device over a relatively long distance. Further, embodiments disclosed herein enable the implantable medical device to be relatively small since a charge storage element of the implantable medical device only needs to be large enough to store enough energy for a single treatment or relatively small number of treatments. Such embodiments may provide effective screening tools to determine whether a particular type of treatment will be effective for a particular patient. For example, vagus nerve stimulation is believed to be effective on about half of a particular candidate patient population. Currently methods of providing vagus nerve stimulation typically involve implanting a medical device in a patient's chest area and running leads under the patient's skin to electrodes implanted in the patient's neck. Since implantable medical devices described herein can be relatively small and may be directly coupled to electrodes, less invasive surgical procedures can be used to implant the implantable medical devices. Thus, these implantable medical devices may be used as screening tools to determine whether vagus nerve stimulation will be effective on a particular patient.

The illustrations of the embodiments described herein are intended to provide a general understanding of the structure of the various embodiments. The illustrations are not intended to serve as a complete description of all of the elements and features of apparatus and systems that utilize the structures or methods described herein. Many other embodiments may be apparent to those of skill in the art upon reviewing the disclosure. Other embodiments may be utilized and derived from the disclosure, such that structural and logical substitutions and changes may be made without departing from the scope of the disclosure. For example, method steps may be performed in a different order than is shown in the figures or one or more method steps may be omitted. Accordingly, the disclosure and the figures are to be regarded as illustrative rather than restrictive.

Moreover, although specific embodiments have been illustrated and described herein, it should be appreciated that any subsequent arrangement designed to achieve the same or similar results may be substituted for the specific embodiments shown. This disclosure is intended to cover any and all subsequent adaptations or variations of various embodiments. Combinations of the above embodiments, and other embodiments not specifically described herein, will be apparent to those of skill in the art upon reviewing the description.

The Abstract of the Disclosure is submitted with the understanding that it will not be used to interpret or limit the scope or meaning of the claims. In addition, in the foregoing Detailed Description, various features may be grouped together or described in a single embodiment for the purpose of streamlining the disclosure. This disclosure is not to be interpreted as reflecting an intention that the claimed embodiments require more features than are expressly recited in each claim. Rather, as the following claims reflect, the claimed subject matter may be directed to less than all of the features of any of the disclosed embodiments.

What is claimed is:

1. An implantable medical device comprising:
   an antenna configured to receive a far field radiative signal;
   a voltage rectifier configured to rectify the far field radiative signal received by the antenna to provide a rectified voltage signal;
   a charge storage element operative to receive the rectified voltage signal and to store charge responsive to the rectified voltage signal;
   a stimulation module powered by the charge storage element, the stimulation module operative to generate an electrical stimulation signal to stimulate a target nerve of a patient;
   control circuitry configured to modulate backscattered energy to encode data in a third order frequency harmonic component of energy backscattered from the implantable medical device; and
   a nerve wrap configured to house the voltage rectifier, the charge storage element, and the stimulation module, wherein the nerve wrap includes one or more electrodes operative to deliver the electrical stimulation signal to the target nerve.

2. The implantable medical device of claim 1, further comprising a flexible printed circuit board, wherein the voltage rectifier, the charge storage element, and the stimulation module are integrated on the flexible printed circuit board.

3. The implantable medical device of claim 2, wherein the antenna is integrated on the flexible printed circuit board.

4. The implantable medical device of claim 2, wherein the flexible printed circuit board is embedded in the nerve wrap.

5. The implantable medical device of claim 4, wherein the one or more electrodes are proximity electrodes, wherein the proximity electrodes are provided on a portion of the nerve wrap, and wherein the nerve wrap is configured to make contact with the target nerve.

6. The implantable medical device of claim 5, wherein the proximity electrodes are printed on the portion of the nerve wrap.

7. The implantable medical device of claim 1, wherein the target nerve is one of a vagus nerve, a trigeminal nerve, a glossopharyngeal nerve, and a hypoglossal nerve.

8. The implantable medical device of claim 1, wherein the charge storage element is one of a capacitor, a capacitor array, a rechargeable battery, and a thin film battery.

9. The implantable medical device of claim 1, further comprising a control unit powered by the charge storage element, the control unit operative to control generation of the electrical stimulation signal by the stimulation module.

10. The implantable medical device of claim 1, wherein the voltage rectifier comprises at least one Schottky diode.

11. The implantable medical device of claim 1, further comprising a threshold detector coupled to the charge storage element, wherein the threshold detector is configured to determine when the charge stored at the charge storage element satisfies a charge threshold, and to provide an indication when the charge threshold is satisfied, and wherein the stimulation module is responsive to the indication.

12. The implantable medical device of claim 11, wherein the antenna is further configured to receive therapy parameter data from an external source, the therapy parameter data including the charge threshold.

13. The implantable medical device of claim 1, wherein the far field radiative signal has a free-space path loss that is proportional to a free-space path distance squared.

14. The implantable medical device of claim 1, wherein the far field radiative signal is a pulsed signal, and wherein the pulsed signal received at the antenna has a power of 100 milliwatts or less during one duty cycle.

15. The implantable medical device of claim 14, wherein each pulse of the far field radiative signal has an instantaneous power selected to reduce a proportion of power lost due to forward biasing components of the voltage rectifier and wherein the instantaneous power of each pulse and an average power of the far field radiative signal are controlled to satisfy respective RF exposure safety limits.

16. The implantable medical device of claim 1, wherein a quantity of the charge stored by the charge storage element enables generation of the electrical stimulation signal for delivery to the target nerve for no more than 24 hours.

17. The implantable medical device of claim 1, wherein a quantity of the charge stored by the charge storage element is not sufficient to enable generation of the electrical stimulation signal for more than a single treatment.

18. The implantable medical device of claim 1, wherein the implantable medical device has a power requirement of 100 microwatts or less to deliver one treatment.

19. The implantable medical device of claim 1, further comprising a receiver coupled to the antenna and configured to receive parameter data, wherein delivery of the electrical stimulation signal to the target nerve is programmed according to the received parameter data.

20. The implantable medical device of claim 1, wherein average input power of the antenna is 53 microwatts or less.

21. The implantable medical device of claim 1, wherein the far field radiative signal has a frequency within a range of approximately 100 MHz to approximately 5.8 GHz.

22. The implantable medical device of claim 1, wherein the voltage rectifier is a multi-stage rectifier.

23. An implantable medical device comprising:
   an antenna configured to receive a far field radiative signal;
   a voltage rectifier configured to rectify the far field radiative signal received by the antenna to provide a rectified voltage signal;
   a charge storage element operative to receive the rectified voltage signal and to store charge responsive to the rectified voltage signal;

a stimulation module powered by the charge storage element, the stimulation module operative to generate an electrical stimulation signal to stimulate a target nerve of a patient;

control circuitry configured to modulate backscattered energy to encode data in energy backscattered from the implantable medical device;

a nerve wrap configured to house the voltage rectifier, the charge storage element, and the stimulation module, wherein the nerve wrap includes one or more electrodes operative to deliver the electrical stimulation signal to the target nerve; and a threshold detector coupled to the charge storage element, wherein the threshold detector is configured to determine when the charge stored at the charge storage element satisfies a charge threshold and to provide an indication when the charge threshold is satisfied, wherein the stimulation module is responsive to the indication, and wherein the antenna is further configured to receive therapy parameter data from an external source, the therapy parameter data including the charge threshold.

24. The implantable medical device of claim 23, further comprising a DC-to-DC converter coupled to the voltage rectifier, wherein the DC-to-DC converter is configured to receive output of a voltage multiplier of the voltage rectifier.

25. The implantable medical device of claim 23, wherein the control circuitry encodes data in a third order frequency harmonic component of the energy backscattered by the implantable medical device.

26. The implantable medical device of claim 25, further comprising a high-Q resonant circuit and amplifier configured to enhance and amplify the third order frequency harmonic component.

27. An implantable medical device comprising:

an antenna configured to receive a far field radiative signal;

a voltage rectifier configured to rectify the far field radiative signal received by the antenna to provide a rectified voltage signal;

a charge storage element operative to receive the rectified voltage signal and to store charge responsive to the rectified voltage signal;

a stimulation module powered by the charge storage element, the stimulation module operative to generate an electrical stimulation signal to stimulate a target nerve of a patient;

control circuitry configured to modulate backscattered energy to encode data in energy backscattered from the implantable medical device; and a nerve wrap configured to house the voltage rectifier, the charge storage element, and the stimulation module, wherein the nerve wrap includes one or more electrodes operative to deliver the electrical stimulation signal to the target nerve, wherein the far field radiative signal is a pulsed signal, wherein the pulsed signal received at the antenna has a power of 100 milliwatts or less during one duty cycle, wherein each pulse of the far field radiative signal has an instantaneous power selected to reduce a proportion of power lost due to forward biasing components of the voltage rectifier and wherein the instantaneous power of each pulse and an average power of the far field radiative signal are controlled to satisfy respective RF exposure safety limits.

* * * * *